US012696684B2

(12) United States Patent
Kim et al.

(10) Patent No.: US 12,696,684 B2
(45) Date of Patent: Jul. 28, 2026

(54) LIGHT EMITTING DEVICE AND DISPLAY DEVICE COMPRISING THE SAME

(71) Applicant: Samsung Display Co., LTD., Yongin-si (KR)

(72) Inventors: Seul Ong Kim, Cheonan-si (KR); Yoonseok Ka, Seoul (KR); Ha Jin Song, Hwaseong-si (KR); Hakchoong Lee, Hwaseong-si (KR); Jae Hoon Hwang, Seoul (KR)

(73) Assignee: Samsung Display Co., Ltd., Yongin-si (KR)

( * ) Notice: Subject to any disclaimer, the term of this patent is extended or adjusted under 35 U.S.C. 154(b) by 974 days.

(21) Appl. No.: 17/900,176

(22) Filed: Aug. 31, 2022

(65) Prior Publication Data

US 2023/0157164 A1 May 18, 2023

(30) Foreign Application Priority Data

Nov. 16, 2021 (KR) ........................ 10-2021-0157789

(51) Int. Cl.
*H10K 85/60* (2023.01)
*C07D 403/04* (2006.01)
(Continued)

(52) U.S. Cl.
CPC ....... *H10K 85/6572* (2023.02); *C07D 403/04* (2013.01); *C09K 11/06* (2013.01);
(Continued)

(58) Field of Classification Search
CPC ............... H10K 85/615; H10K 85/654; H10K 85/6572; H10K 50/19; C07D 251/24
See application file for complete search history.

(56) References Cited

U.S. PATENT DOCUMENTS

| | | | | |
|---|---|---|---|---|
| 2017/0047524 A1 | 2/2017 | Kim et al. | | |
| 2020/0131133 A1* | 4/2020 | La | ........................ | H10K 85/622 |
| 2021/0273192 A1* | 9/2021 | Kim | ..................... | H10K 50/131 |

FOREIGN PATENT DOCUMENTS

| | | |
|---|---|---|
| KR | 10-2015-0014380 | 2/2015 |
| KR | 10-2015-0124886 A | 11/2015 |

(Continued)

OTHER PUBLICATIONS

Extended European Search Report issued in corresponding EP Application No. 10-2021-0157789, dated Jul. 10, 2025 (9 pages).

(Continued)

*Primary Examiner* — Vu A Nguyen
(74) *Attorney, Agent, or Firm* — Womble Bond Dickinson (US) LLP

(57) ABSTRACT

An embodiment of the present invention provides a light-emitting device including: a first electrode; a second electrode configured to overlap the first electrode; m emission units positioned between the first electrode and the second electrode; and (m−1) charge generating layers disposed between adjacent emission units, wherein each of the charge generating layers includes an n-type charge generating layer and a p-type charge generating layer, and the n-type charge
(Continued)

generating layer contains a compound represented by the following Chemical Formula 1:

[Chemical Formula 1]

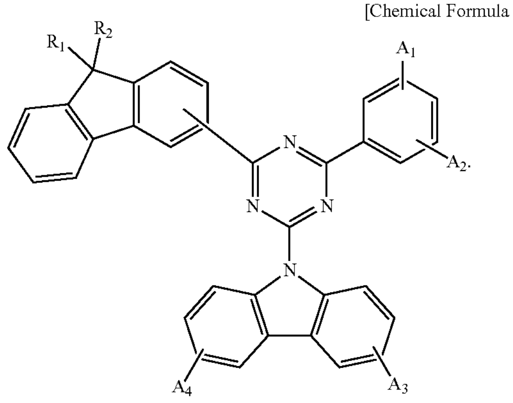

18 Claims, 7 Drawing Sheets

(51) Int. Cl.

| | |
|---|---|
| ***C09K 11/06*** | (2006.01) |
| ***H10K 50/11*** | (2023.01) |
| ***H10K 50/16*** | (2023.01) |
| ***H10K 50/17*** | (2023.01) |
| ***H10K 50/19*** | (2023.01) |
| ***H10K 59/12*** | (2023.01) |
| ***H10K 101/30*** | (2023.01) |
| ***H10K 102/00*** | (2023.01) |

(52) U.S. Cl.

CPC ......... *H10K 85/615* (2023.02); *H10K 85/654* (2023.02); *C09K 2211/1018* (2013.01); *H10K 50/11* (2023.02); *H10K 50/16* (2023.02); *H10K 50/171* (2023.02); *H10K 50/19* (2023.02); *H10K 59/12* (2023.02); *H10K 2101/30* (2023.02); *H10K 2102/351* (2023.02)

(56) References Cited

FOREIGN PATENT DOCUMENTS

| | | | |
|---|---|---|---|
| KR | 10-2017-0023328 | 3/2017 | |
| KR | 10-2018-0063708 A | 6/2018 | |
| KR | 10-1908509 | 10/2018 | |
| KR | 10-2021-0033332 | 3/2021 | |
| WO | WO-2015167199 A1 * | 11/2015 | ........... C07D 405/14 |

OTHER PUBLICATIONS

G. Parthasarathy et al., "Lithium doping of semiconducting organic charge transport materials", Journal of Applied Physics, May 1, 2001, 8 total pages, vol. 89, No. 9.

* cited by examiner

LIGHT EMITTING DEVICE AND DISPLAY DEVICE COMPRISING THE SAME

CROSS REFERENCE TO RELATED APPLICATION(S)

This application claims priority to and benefits of Korean Patent Application No. 10-2021-0157789, under 35 U.S.C. § 119, filed on Nov. 16, 2021, in the Korean Intellectual Property Office (KIPO) the entire contents of which are incorporated herein by reference.

BACKGROUND

1. Technical Field

The disclosure relates to a light-emitting device and a display device including the same.

2. Description of the Related Art

A light-emitting device is a device having a characteristic in which electrical energy is converted into light energy. Examples of such a light-emitting device include an organic light emitting element using an organic material for an emission layer, and a quantum dot light emitting device using quantum dots for an emission layer.

The light-emitting device may include a first electrode and a second electrode overlapping each other, a hole transport region positioned therebetween, an emission layer, and an electron transport region. Holes injected into the first electrode move to the emission layer through the hole transport region, and electrons injected into the second electrode move to the emission layer through the electron transport region. Holes and electrons combine to form excitons in an emission layer region. Light is generated as the excitons change from an excited state to a ground state.

The above information disclosed in this Background section is only for enhancement of understanding of the background of the disclosure, and therefore, it may contain information that does not form the prior art that is already known in this country to a person of ordinary skill in the art.

SUMMARY

The disclosure has been made in an effort to provide a light-emitting device capable of simplifying a manufacturing process. Further, the disclosure has been made in an effort to provide a light-emitting device having improved luminous efficiency and lifetime. The disclosure has been made in an effort to provide a light-emitting device having a reduced leakage current, and a display device including the same and having improved display quality.

A light-emitting device may include: a first electrode; a second electrode that overlaps the first electrode; m emission parts positioned between the first electrode and the second electrode; and (m−1) charge generating layers disposed between adjacent emission parts, wherein each of the charge generating layers may include an n-type charge generating layer and a p-type charge generating layer, and the n-type charge generating layer may include a compound represented by Chemical Formula 1:

[Chemical Formula 1]

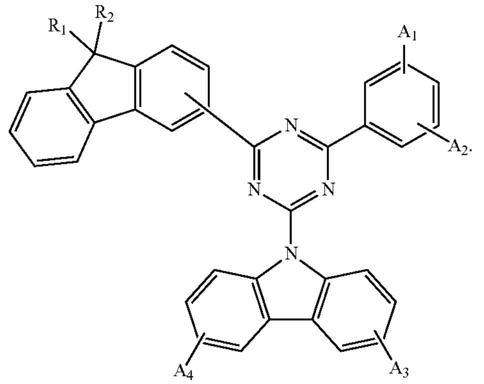

In Chemical Formula 1, $R_1$ and $R_2$ may each independently include an aliphatic compound, an aromatic compound, or a hetero compound having 1 to 30 carbon atoms, $A_1$, $A_2$, $A_3$, and $A_4$ each may independently include: hydrogen, an aliphatic compound, an aromatic compound, or a hetero compound; or an aliphatic compound, an aromatic compound, or a hetero compound, each substituted with at least one of CN, F, or CF3, and m may be a natural number that is greater than or equal to 2.

The n-type charge generating layer may not contain an inorganic material.

A lowest unoccupied molecular orbital (LUMO) energy level of the n-type charge generating layer may be in a range of about −2.8 eV to about −3.4 eV.

The compound represented by Chemical Formula 1 may include at least one of compounds represented by Chemical Formula 1-1 to Chemical Formula 1-4 below.

[Chemical Formula 1-1]

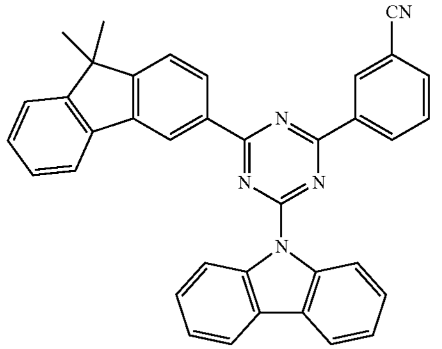

[Chemical Formula 1-2]

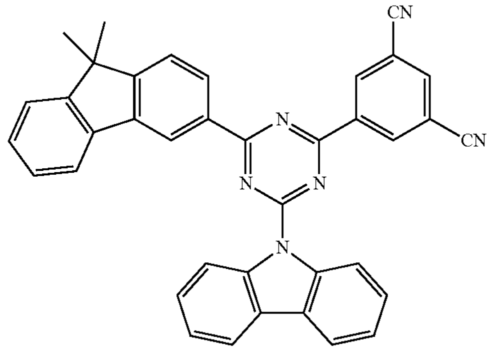

-continued

[Chemical Formula 1-3]

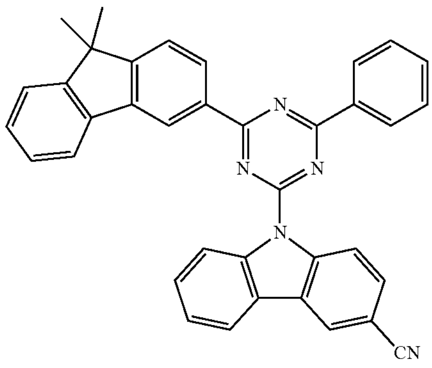

[Chemical Formula 1-4]

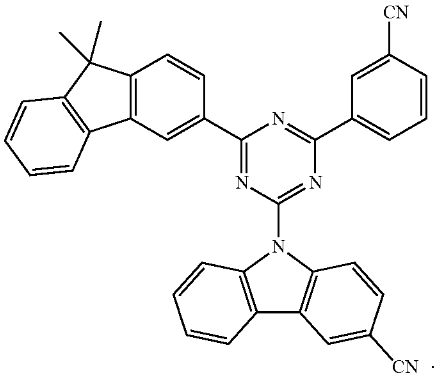

The n-type charge generating layer may include at least two sub n-type charge generating layers.

The n-type charge generating layer may include a first sub n-type charge generating layer and a second sub n-type charge generating layer.

Each of the emission part may include a first emission part and a second emission part, the first sub n-type charge generating layer may be positioned adjacent to the first emission part, and the second sub n-type charge generating layer may be positioned adjacent to the second emission part.

A lowest unoccupied molecular orbital (LUMO) energy level value of the first sub n-type charge generating layer may be greater than a LUMO energy level value of the second sub n-type charge generating layer.

A light-emitting device may include: a first electrode; a second electrode that overlaps the first electrode; m emission parts positioned between the first electrode and the second electrode; and (m−1) charge generating layers disposed between adjacent emission parts, wherein each of the emission part may include a hole transport region, an electron transport region, and an emission layer positioned between the hole transport region and the electron transport region, and the electron transport region may include a compound represented by Chemical Formula 1:

[Chemical Formula 1]

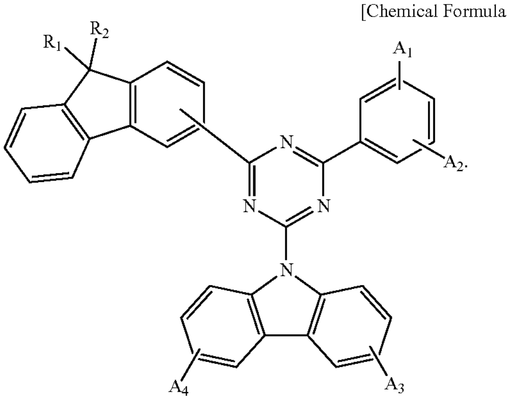

In Chemical Formula 1, $R_1$ and $R_2$ each may independently include an aliphatic compound, an aromatic compound, or a hetero compound having 1 to 30 carbon atoms, $A_1$, $A_2$, $A_3$, and $A_4$ each may independently include: hydrogen, an aliphatic compound, an aromatic compound, or a hetero compound; or an aliphatic compound, an aromatic compound, or a hetero compound each substituted with at least one of CN, F, or CF3, and m may be a natural number that is greater than or equal to 2.

The electron transport region may include an electron injection layer and an electron transport layer, and the electron injection layer may include the compound represented by Chemical Formula 1.

The electron injection layer may not contain an inorganic material.

A lowest unoccupied molecular orbital (LUMO) energy level of the electron injection layer may be in a range of about −2.8 eV to about −3.4 eV.

A display device may include: a transistor disposed on a substrate; and a light emitting device electrically connected to the transistor, wherein the light-emitting device may include: a first electrode; a second electrode that overlaps the first electrode; m emission parts positioned between the first electrode and the second electrode; and (m−1) charge generating layers disposed between adjacent emission parts, each of the charge generating layers may include an n-type charge generating layer and a p-type charge generating layer, and the n-type charge generating layer may include a compound represented by Chemical Formula 1:

[Chemical Formula 1]

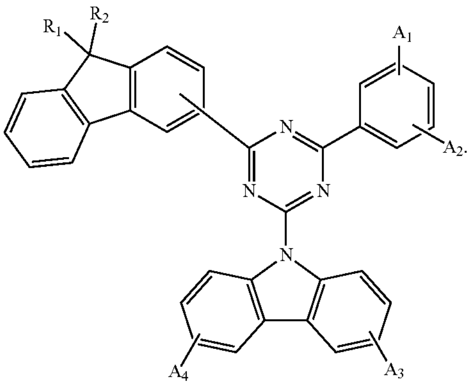

In Chemical Formula 1, $R_1$ and $R_2$ each may independently include an aliphatic compound, an aromatic compound, or a hetero compound having 1 to 30 carbon atoms, $A_1$, $A_2$, $A_3$, and $A_4$ each may independently include: hydrogen, an aliphatic compound, an aromatic compound, or a hetero compound; or an aliphatic compound, an aromatic compound, or a hetero compound each substituted with at least one of CN, F, or CF3, and m may be a natural number that is greater than or equal to 2.

The n-type charge generating layer may not contain an inorganic material.

A lowest unoccupied molecular orbital (LUMO) energy level of the n-type charge generating layer may be in a range of about −2.8 eV to about −3.4 eV.

The n-type charge generating layer may include at least two sub n-type charge generating layers.

The n-type charge generating layer may include a first sub n-type charge generating layer and a second sub n-type charge generating layer.

Each of the emission part may include a first emission part and a second emission part, the first sub n-type charge generating layer may be positioned adjacent to the first emission part, and the second sub n-type charge generating layer may be positioned adjacent to the second emission part.

A lowest unoccupied molecular orbital (LUMO) energy level value of the first sub n-type charge generating layer may be greater than a LUMO energy level value of the second sub n-type charge generating layer.

The emission part may include a hole transport region, an electron transport region, and an emission layer positioned between the hole transport region and the electron transport region, the electron transport region may include an electron injection layer and an electron transport layer, and the electron injection layer may include the compound represented by Chemical Formula 1.

According to the embodiments, it is possible to provide a light-emitting device capable of simplifying a manufacturing process. Further, it is possible to provide a light-emitting device having improved luminous efficiency and lifetime. It is possible to provide a light-emitting device having a reduced leakage current, and a display device including the same and having improved display quality.

DETAILED DESCRIPTION OF THE EMBODIMENTS

Figure 1:
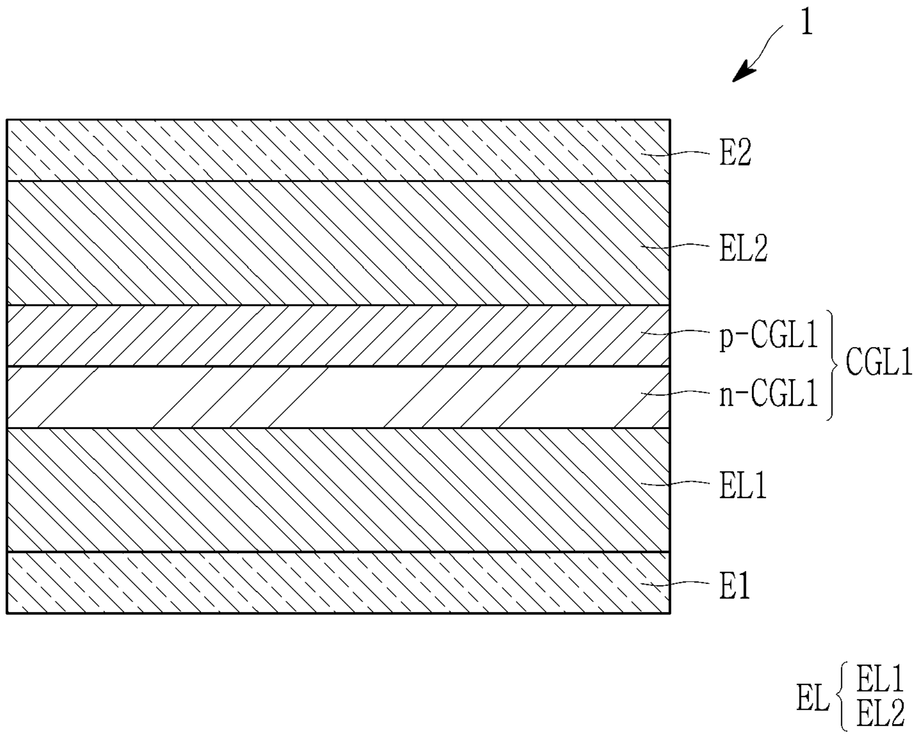
FIG. 1 illustrates a schematic cross-sectional view of a light-emitting device according to an embodiment.

The disclosure will be described more fully hereinafter with reference to the accompanying drawings, in which embodiments of the disclosure are shown. As those skilled in the art would realize, the described embodiments may be modified in various different ways, all without departing from the spirit or scope of the disclosure.

To clearly describe the disclosure, parts that are irrelevant to the description are omitted, and like numerals refer to like or similar constituent elements throughout the specification.

Further, since sizes and thicknesses of constituent members shown in the accompanying drawings are arbitrarily given for better understanding and ease of description, the disclosure is not limited to the illustrated sizes and thicknesses. In the drawings, the thicknesses of layers, films, panels, regions, etc., are exaggerated for clarity. In the drawings, for better understanding and ease of description, the thicknesses of some layers and areas are exaggerated.

It will be understood that when an element such as a layer, film, region, or substrate is referred to as being "on" another element, it can be directly on the other element or intervening elements may also be present. In contrast, when an element is referred to as being "directly on" another element, there are no intervening elements present. Further, in the specification, the word "on" or "above" means positioned on or below the object portion, and does not necessarily mean positioned on the upper side of the object portion based on a gravitational direction.

In addition, unless explicitly described to the contrary, the word "comprise" and variations such as "comprises" or "comprising" will be understood to imply the inclusion of stated elements but not the exclusion of any other elements.

Further, in the specification, the phrase "in a plan view" means when an object portion is viewed from above, and the phrase "in a cross-sectional view" means when a cross-section taken by vertically cutting an object portion is viewed from the side.

In the specification and the claims, the phrase "at least one of" is intended to include the meaning of "at least one selected from the group of" for the purpose of its meaning and interpretation. For example, "at least one of A and B" may be understood to mean "A, B, or A and B."

In the specification and the claims, the term "and/or" is intended to include any combination of the terms "and" and "or" for the purpose of its meaning and interpretation. For example, "A and/or B" may be understood to mean "A, B, or A and B." The terms "and" and "or" may be used in the conjunctive or disjunctive sense and may be understood to be equivalent to "and/or."

In the description, it will be understood that when an element (or region, layer, part, etc.) is referred to as being "on", "adjacent to", "connected to", or "coupled to" another element, it can be directly on, adjacent to, connected to, or coupled to the other element, or one or more intervening elements may be present therebetween. In a similar sense, when an element (or region, layer, part, etc.) is described as "covering" another element, it can directly cover the other element, or one or more intervening elements may be present therebetween.

In the description, when an element is "directly on," "directly adjacent to," "directly connected to," or "directly coupled to" another element, there are no intervening elements present. For example, "directly on" may mean that two layers or two elements are disposed without an additional element such as an adhesion element therebetween.

In the specification, "(intermediate layer) includes a compound represented by Chemical Formula 1" may be interpreted as "(intermediate layer) may include one compound belonging to the category of Chemical Formula 1 or two or more different compounds belonging to the category of Chemical Formula 1."

In this specification, "Group" indicates a group on the IUPAC periodic table of elements.

In this specification, "alkali metal" indicates a Group 1 element. Specifically, the alkali metal may be lithium (Li), sodium (Na), potassium (K), rubidium (Rb), or cesium (Cs).

In this specification, "alkaline earth metal" indicates a Group 2 element. Specifically, the alkaline earth metal may be magnesium (Mg), calcium (Ca), strontium (Sr), or barium (Ba).

In the specification, "lanthanum metal" indicates lanthanum and a lanthanum group element in the periodic table. Specifically, a metal of the lanthanum group may be lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), or ruthenium (Ru).

In this specification, "transition metal" refers to elements belonging to Groups 3 to 12 while belonging to cycle 4 to cycle 7. Specifically, the transition metal may be titanium (Ti), zirconium (Zr), hafnium (Hf), vanadium (V), niobium (Nb), tantalum (Ta), chromium (Cr), molybdenum (Mo), tungsten (W), manganese (Mn), technetium (Tc), rhenium (Re), iron (Fe), ruthenium (Ru), osmium (Os), cobalt (Co), rhodium (Rh), iridium (Ir), nickel (Ni), palladium (Pd), platinum (Pt), copper (Cu), silver (Ag), gold (Au), zinc (Zn), or cadmium (Cd).

In this specification, "post-transition metal" refers to elements belonging to Groups 13 to 17 while belonging to cycle 4 to cycle 7. Specifically, the post-transition metal may be aluminum (Al), gallium (Ga), indium (In), thallium (Tl), tin (Sn), lead (Pb), bismuth (Bi), or polonium (Po).

In this specification, "halogen" indicates a Group 17 element. Specifically, the halogen may be fluorine (F), chlorine (Cl), bromine (Br), or iodine (I).

In the specification, the term "inorganic semiconductor compound" refers to any compound that is an inorganic material and has a band gap of less than 4 eV. Specifically, the inorganic semiconductor compounds may include a lanthanide metal halide, a transition metal halide, a post-transition metal halide, tellurium, a lanthanide metal telluride, a transition metal telluride, a post-transition metal telluride, a selenide of a lanthanide group metal, a selenide of a transition metal, a selenide of a post-transition metal, or any combination thereof. More specifically, the inorganic semiconductor compound may include $EuI_2$, $YbI_2$, $SmI_2$, $TmI_2$, AgI, CuI, $NiI_2$, $CoI_2$, $BiI_3$, $PbI_2$, $SnI_2$, Te, EuTe, YbTe, SmTe, TmTe, EuSe, YbSe, SmSe, TmSe, ZnTe, CoTe, ZnSe, CoSe, $Bi_2Te_3$, $Bi_2Se_3$, or any combination thereof.

In the specification, "inorganic insulator compound" refers to all compounds that are inorganic and have a band gap of 4 eV or more. Specifically, the inorganic insulator compound may include a halide of an alkali metal, a halide of an alkaline earth metal, a halide of a lanthanide metal, or any combination thereof. More specifically, the inorganic insulator compound may include NaI, KI, RbI, CsI, NaCl, KCl, RbCl, CsCl, NaF, KF, RbF, CsF, $MgI_2$, $CaI_2$, $SrI_2$, $BaI_2$, $MgCl_2$, $CaCl_2$, $SrCl_2$, $BaCl_2$, $MgF_2$, $CaF_2$, $SrF_2$, $BaF_2$, $EuI_3$, $YbI_3$, $SmI_3$, $TmI_3$, $EuCl_3$, $YbCl_3$, $SmCl_3$, $TmCl_3$, $EuF_3$, $YbF_3$, $SmF_3$, $TmF_3$, or any combination thereof.

In the specification, "halide of an alkali metal" refers to a compound in which an alkali metal and a halogen are ionically bonded. Specifically, the halide of the alkali metal may include NaI, KI, RbI, CsI, NaCl, KCl, RbCl, CsCl, NaF, KF, RbF, CsF, or any combination thereof.

In this specification, "halide of an alkaline earth metal" refers to a compound in which an alkaline earth metal and a halogen are ionically bonded. Specifically, the halide of an alkaline earth metal may include $MgI_2$, $CaI_2$, $SrI_2$, $BaI_2$, $MgCl_2$, $CaCl_2$, $SrCl_2$, $BaCl_2$, $MgF_2$, $CaF_2$, $SrF_2$, $BaF_2$, or any combination thereof.

In the specification, "halide of a lanthanum group metal" refers to a compound in which a lanthanum group metal and a halogen are ionically and/or covalently bonded. Specifically, the halide of the lanthanide metal may include $EuI_2$, $YbI_2$, $SmI_2$, $TmI_2$, $EuI_3$, $YbI_3$, $SmI_3$, $TmI_3$, $EuCl_3$, $YbCl_3$, $SmCl_3$, $TmCl_3$, $EuF_3$, $YbF_3$, $SmF_3$, $TmF_3$, or any combination thereof.

In the specification, "halide of a transition metal" refers to a compound in which a transition metal and a halogen are ionically and/or covalently bonded. Specifically, the halide of the transition metal may include AgI, CuI, $NiI_2$, $CoI_2$, or any combination thereof.

In the specification, "halide of a post-transition metal" refers to a compound in which a post-transition metal and a halogen are ionically and/or covalently bonded. Specifically, the halide of the post-transition metal may include $BiI_3$, $PbI_2$, $SnI_2$, or any combination thereof.

In the specification, "telluride of a lanthanum group metal" refers to a compound in which a lanthanum group metal and tellurium (Te) are ionically, covalently, and/or metallically bonded. Specifically, the telluride of the lanthanum metal may include EuTe, YbTe, SmTe, TmTe, or any combination thereof.

In the specification, "transition metal telluride" refers to a compound in which a transition metal and tellurium are ionically, covalently, and/or metallically bonded. Specifically, the telluride of the transition metal may include ZnTe, CoTe, or any combination thereof.

In the specification, "post-transition metal telluride" refers to a compound in which a post-transition metal and tellurium are ionically, covalently, and/or metallically bonded. Specifically, the telluride of the post-transition metal may include $Bi_2Te_3$.

In the specification, "selenide of lanthanide metal" refers to a compound in which lanthanum metal and cell rhenium (Se) are ionically, covalently, and/or metallically bonded. Specifically, the selenide of the lanthanum metal may include EuSe, YbSe, SmSe, TmSe, or any combination thereof.

In the specification, "selenide of a transition metal" refers to a compound in which a transition metal and selenium are ionically, covalently, and/or metallically bonded. Specifically, the selenide of the transition metal may include ZnSe, CoSe, or any combination thereof.

In the specification, "selenide of a post-transition metal" refers to a compound in which a post-transition metal and selenium are ionically, covalently, and/or metallically bonded. Specifically, the selenide of the post-transition metal may include $Bi_2Se_3$.

Figure 2:
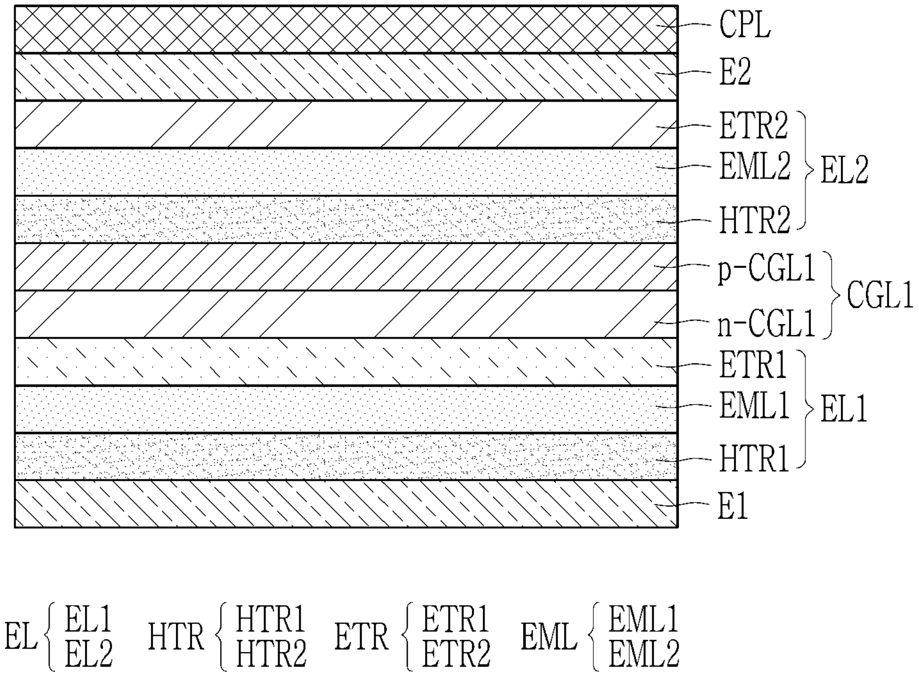
FIG. 2 illustrates a schematic cross-sectional view of a light-emitting device according to an embodiment.

Hereinafter, a light-emitting device according to an embodiment will be described with reference to FIG. 1 and FIG. 2. FIG. 1 illustrates a schematic cross-sectional view of a light-emitting device according to an embodiment, and FIG. 2 illustrates a schematic cross-sectional view of a light-emitting device according to an embodiment.

First of all, referring to FIG. 1, the light-emitting device 1 may include a first electrode E1, a second electrode E2, and multiple emission parts EL positioned between the first electrode E1 and the second electrode E2.

The light-emitting device 1 according to an embodiment of the disclosure may be a top emission type. The first electrode E1 may be an anode, and the second electrode E2 may be a cathode. The light-emitting device 1 according to another embodiment of the disclosure may be a bottom emission type. The first electrode E1 may be a cathode, and the second electrode E2 may be an anode. In the light-emitting device 1 according to an embodiment of the disclosure, the first electrode E1 may be a reflective electrode, and the second electrode E2 may be a transmissive or transflective electrode, and the light-emitting device 1 may emit light in a direction from the first electrode E1 to the second electrode E2. Hereinafter, a case in which the light-emitting device is the top emission type will be described.

The first electrode E1 may be formed by, e.g., providing a material for the first electrode at an upper portion of a substrate by using a deposition method, such as a sputtering method, or the like. In case that the first electrode E1 is an anode, the material for the first electrode may be selected from among materials having a high work function to facilitate hole injection.

The first electrode E1 may be a reflective electrode, a transflective electrode, or a transmissive electrode. The material for the first electrode may be selected from among an indium tin oxide (ITO), an indium zinc oxide (IZO), a tin oxide ($SnO_2$), a zinc oxide (ZnO), and any combination thereof in order to form the first electrode E1 which is a transmissive electrode, but the disclosure is not limited thereto. As another example, the material for the first electrode may be selected from among magnesium (Mg), silver (Ag), aluminum (Al), aluminum-lithium (Al—Li), calcium (Ca), magnesium-indium (Mg—In), magnesium-silver (Mg—Ag), and any combination thereof in order to form the first electrode E1, which is a transflective electrode or a reflective electrode, but the disclosure is not limited thereto.

The first electrode E1 may have a single-layer structure that is a single layer or a multi-layered structure having multiple layers. For example, the first electrode E1 may have a three-layer structure of ITO/Ag/ITO, but the disclosure is not limited thereto.

M number of emission parts EL may be positioned on the first electrode E1. M is a natural number that is greater than or equal to 2. The light-emitting device 1 according to an embodiment may include at least two emission parts EL. The light-emitting device 1 according to an embodiment may include a first emission part EL1 and a second emission part EL2, but the disclosure is not limited thereto.

The light-emitting device 1 according to an embodiment may include a charge generating layer CGL1 positioned between adjacent emission parts EL. The charge generating layer CGL1 may generate charges (electrons and holes) by forming a complex through an oxidation-reduction reaction in case that a voltage is applied thereto. The charge generating layer CGL1 may provide the generated charges to the adjacent emission part EL.

The charge generating layer CGL1 may double current efficiency generated by the emission part EL, and may serve to adjust balance of charges between the adjacent emission parts EL.

In case that the light-emitting device 1 includes m emission parts EL, the light-emitting device 1 may include (m−1) charge generating layers CGL1 provided between the adjacent emission parts EL. The light-emitting device 1 according to an embodiment may include a first charge generating layer CGL1 positioned between the first emission part EL1 and the second emission part EL2. Although the specification shows the embodiment including one charge generating layer CGL1, the disclosure is not limited thereto, and may vary depending on the number of emission parts EL.

Each charge generating layer CGL1 may include an n-type charge generating layer n-CGL1 that provides electrons to the emission part EL and a p-type charge generating layer p-CGL1 that provides holes to the emission part EL. Although not illustrated, a buffer layer may be further disposed between the n-type charge generating layer n-CGL1 and the p-type charge generating layer p-CGL1 according to an embodiment. The n-type charge generating layer n-CGL1 may be disposed adjacent to the first emission part EL1, and the p-type charge generating layer p-CGL1 may be disposed adjacent to the second emission part EL2.

The n-type charge generating layer n-CGL1 may include a compound represented by Chemical Formula 1 below.

[Chemical Formula 1]

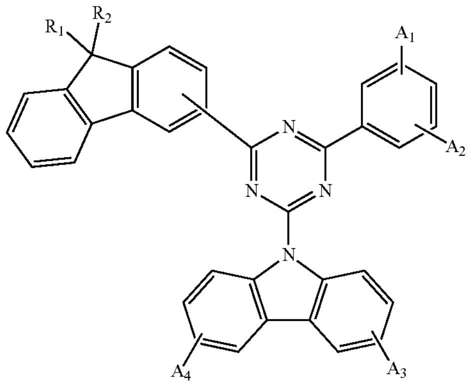

In Chemical Formula 1, each of $R_1$ and $R_2$ may independently include an aliphatic compound, an aromatic compound, or a hetero compound having 1 to 30 carbon atoms, and each of $A_1$, $A_2$, $A_3$, and $A_4$ may independently include hydrogen, an aliphatic compound, an aromatic compound, or a hetero compound, or an aliphatic compound, an aromatic compound, or a hetero compound each substituted with at least one of CN, F, or CF3.

The n-type charge generating layer n-CGL1 according to an embodiment may be formed of an organic compound represented by Chemical Formula 1. The n-type charge generating layer n-CGL1 may not include a separate inorganic material.

A lowest unoccupied molecular orbital (LUMO) energy level of the n-type charge generating layer n-CGL1 according to an embodiment may be in a rage of about −2.8 eV to about −3.4 eV. An absolute value of the LUMO energy level of the n-type charge generating layer n-CGL1 according to an embodiment may be greater than that of a LUMO energy level of an electron transport region, which will be described later. It may readily provide electrons to the emission part EL by providing the n-type charge generating layer n-CGL1 having a relatively large absolute value of the LUMO energy level. For example, in Chemical Formula 1, $A_1$ and $A_2$ may each be a main component that determines the LUMO energy level value of the n-type charge generating layer n-CGL1. In Chemical Formula 1, $A_1$ and $A_2$ may each be a substituent that attracts electrons. As the electron-attracting force of each of $A_1$ and $A_2$ increases, the LUMO energy level value of the n-type charge generating layer n-CGL1 may be lowered, and an absolute value of the LUMO energy level of the n-type charge generating layer n-CGL1 may be increased.

The compound represented by Chemical Formula 1 constituting the n-type charge generating layer n-CGL1 according to an embodiment may include a carbazole-based compound. The carbazole-based compound may increase a dipole moment of the compound expressed by Chemical Formula 1. As the dipole moment of the compound expressed by Chemical Formula 1 increases, electrons may readily move from the p-type charge generating layer p-CGL1 to the n-type charge generating layer n-CGL1. The dipole moment of the compound represented by the Chemical Formula 1 according to an embodiment may be about 2.0 debyes or more.

The compound represented by Chemical Formula 1 constituting the n-type charge generating layer n-CGL1 according to an embodiment may include a triazine-based compound. Electron mobility of the n-type charge generating layer n-CGL1 may be improved by the triazine-based compound.

The compound represented by Chemical Formula 1 constituting the n-type charge generating layer n-CGL1 according to an embodiment may include a functional group having $R_1$ and $R_2$. The functional group having $R_1$ and $R_2$ may be relatively bulky, and the n-type charge generating layer n-CGL1 including the compound represented by Chemical Formula 1 may have an amorphous characteristic.

The n-type charge generating layer n-CGL1 according to an embodiment may be individually formed of an organic compound represented by Chemical Formula 1. Since the n-type charge generating layer n-CGL1 is made of a single compound, it may be formed using one deposition head. An n-type charge generating layer n-CGL1 including two or more compounds may be formed using an angle limiting plate for co-evaporation. However, since the n-type charge generating layer n-CGL1 according to an embodiment is formed using one deposition head, a manufacturing process may be simplified and a manufacturing cost may be reduced.

The compound represented by Chemical Formula 1 may be represented by following Chemical Formula 1-1 to Chemical Formula 1-4.

[Chemical Formula 1-1]

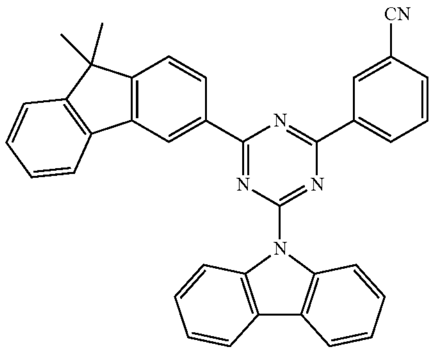

[Chemical Formula 1-2]

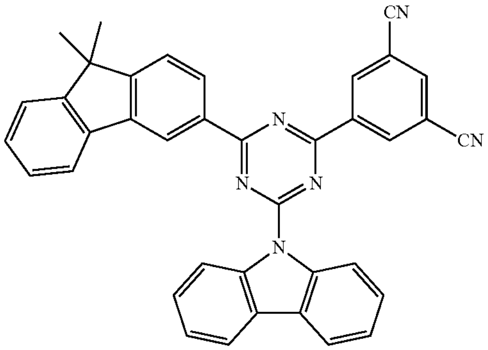

-continued

[Chemical Formula 1-3]

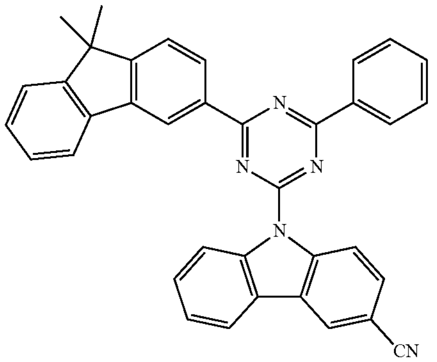

[Chemical Formula 1-4]

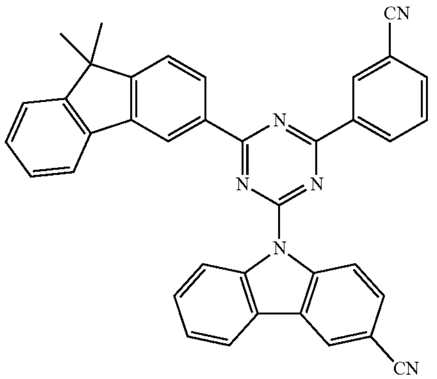

The n-type charge generating layer n-CGL1 according to an embodiment may not include an inorganic material. In the case of the n-type charge generating layer n-CGL1 formed by doping an inorganic material, a leakage current may flow to an adjacent light-emitting device in a horizontal direction. Accordingly, color mixture may be caused by emitting light on other light-emitting devices where no voltage is applied. Since the n-type charge generating layer n-CGL1 according to an embodiment does not include an inorganic material, it may be possible to control the current leakage and unintentional light emission of the light-emitting device. A light-emitting device including an n-type charge generating layer n-CGL1 according to an embodiment and a display panel including the same may improve display quality without color mixing.

The p-type charge generating layer p-CGL1 may include a hole transporting organic compound, an inorganic insulator compound, or any combination thereof. For a description of the hole transporting organic compound, refer to the following description. The p-type charge generating layer p-CGL1 may include at least one inorganic semiconductor compound. A thickness of the p-type charge generating layer p-CGL1 may be about 0.1 nm to about 20 nm.

The second electrode E2 is positioned on an $m^{th}$ emission part EL. The second electrode E2 may be a cathode that is an electron injection electrode, and a material for the second electrode E2 may include a metal, an alloy thereof, an electrically conductive compound, and a combination thereof, having a low work function.

The second electrode E2 may include at least one selected from a group of lithium (Li), silver (Ag), magnesium (Mg), aluminum (Al), ytterbium (Yb), aluminum-lithium (Al—Li), calcium (Ca), magnesium-indium (Mg—In), silver-magnesium (Ag—Mg), silver-ytterbium (Ag—Yb), ITO, and IZO, but the disclosure is not limited thereto. The second electrode E2 may be a transmissive electrode, a transflective electrode, or a reflective electrode.

The second electrode E2 may have a single-layer structure that is a single layer or a multi-layered structure having multiple layers.

A thickness of the second electrode E2 may be about 5 nm to about 20 nm. In case that the above-described range is satisfied, light absorption at the second electrode may be minimized, and a satisfactory electron injection characteristic may be obtained without a substantial increase in driving voltage.

Hereinafter, a detailed stacked structure of each emission part EL according to an embodiment will be described with reference to FIG. 2. An embodiment of the light-emitting device with two emission parts EL will be described. A description of the above-described constituent element will be omitted.

Each emission part EL may include an emission layer EML. Each emission part EL may also include at least one of a hole transport region HTR and an electron transport region ETR. The hole transport region HTR may include a hole injection layer, a hole transport layer, an electron blocking layer, or any combination thereof. The electron transport region ETR may include a hole blocking layer, an electron transport layer, an electron injection layer, or any combination thereof. Each of the emission parts EL may include an emission layer EML, a hole transport region HTR, an electron transport region ETR including different materials, or an emission layer EML, a hole transport region HTR, and an electron transport region ETR including a same material.

The first emission part EL1 may include a first emission layer EML1 that emits light, a first hole transport region HTR1 that transports holes supplied from the first electrode E1 to the first emission layer EML1, and a first electron transport region ETR1 that transports electrons generated from a first charge generating layer CGL1 to the first emission layer EML1

The second emission part EL2 may include a second emission layer EML2 that emits light, a second hole transport region HTR2 that transports holes supplied from the first charge generating layer CGL1 to the second emission layer EML2, and a second electron transport region ETR2 that transports electrons to the second emission layer EML2.

The hole transport region HTR may be formed using a general method. For example, the hole transport region HTR may be formed by using a variety of methods such as vacuum deposition, spin coating, casting, a Langmuir-Blodgett (LB) technique, inkjet printing, laser printing, and laser induced thermal imaging (LITI).

The hole injection layer included in the hole transport region HTR may include a hole injection material. The hole injection material may include a phthalocyanine compound such as copper phthalocyanine; DNTPD (N,N'-diphenyl-N,N'-bis-[4-(phenyl-m-tolyl-amino)-phenyl]-biphenyl-4,4'-diamine), m-MTDATA (4,4',4"-[tris(3-methylphenyl)phenylamino]triphenylamine), TDATA (4,4'4"-tris(N,N-diphenylamino)triphenylamine), 2-TNATA (4,4',4"-tris{N,-(2-naphthyl)-N-phenylamino}-triphenylamine), PEDOT/PSS (poly(3,4-ethylenedioxythiophene)/poly(4-styrenesulfonate)), PANI/DBSA (polyaniline/dodecylbenzenesulfonic acid), PANI/CSA (polyaniline/camphor sulfonic acid), PANI/PSS (polyaniline/poly(4-styrenesulfonate)), NPB (N,N'-di(naphthalene-1-yl)-N,N'-diphenyl-benzidine), NPD (N,N'-Di(1-naphthyl)-N,N'-diphenyl-(1,1'-biphenyl)-4,4'-diamine), polyether ketone containing triphenylamine (TPAPEK), 4-Isopropyl-4'-methyldiphenyliodonium [tetrakis(pentafluorophenyl)borate], HAT-CN (dipyrazino[2,3-f:2',3'-h]quinoxaline-2,3,6,7,10,11-hexacarbonitrile), and the like.

The hole transport layer included in the hole transport region HTR may include a hole transport material. The hole transport material may include a carbazole-based derivative such as N-phenylcarbazole and polyvinylcarbazole, a fluorene-based derivative, TPD (N,N'-bis(3-methylphenyl)-N,N'-diphenyl-[triphenylamine derivatives such as 1,1-biphenyl]-4,4'-diamine), TCTA (4,4',4"-tris(N-carbazolyl) triphenylamine), NPB (N,N'-di(naphthalene-1-yl)-N,N'-diphenyl-benzidine), TAPC (4,4'-cyclohexylidene bis[N,N-bis(4-methylphenyl)benzenamine]), HMTPD (4,4'-bis[N,N'-(3-tolyl)amino]-3,3'-dimethylbiphenyl), mCP (1,3-bis(N-carbazolyl)benzene), CzSi (9-(4-tert-butylphenyl)-3,6-bis(triphenylsilyl)-9H-carbazole), m-MTDATA (4,4',4"-[tris(3-methylphenyl)phenylamino]triphenylamine), or the like.

A thickness of the hole transport region HTR may be about 100 Å to about 10000 Å, e.g., about 100 Å to about 5000 Å. For example, the thickness of the hole injection layer may be about 30 Å to about 1000 Å, and the thickness of the hole transport layer may be about 30 Å to about 1000 Å. In case that thicknesses of the hole transport region HTR, the hole injection layer, and the hole transport layer satisfy the above-described ranges, a satisfactory hole transport characteristic may be obtained without a substantial increase in driving voltage.

The electron blocking layer may be a layer that prevents electrons from leaking from the electron transport region ETR to the hole transport region HTR. A thickness of the electron blocking layer may be about 10 Å to about 1000 Å. The electron blocking layer may include, e.g., a carbazole-based derivative such as N-phenylcarbazole or polyvinylcarbazole, a fluorene-based derivative, or TPD (N,N'-bis(3-methylphenyl)-N,N'-diphenyl-triphenylamine derivatives such as [1,1-biphenyl]-4,4'-diamine), TCTA (4,4',4"-tris(N-carbazolyl)triphenylamine), NPD (N,N'-di(naphthalene-1-yl)-N,N'-diphenyl-benzidine), TAPC (4,4'-[N,N-bis(4-methylphenyl)benzenamine]), HMTPD (4,4'-bis[N,N'-(3-tolyl)amino]-3,3'-dimethylbiphenyl), mCP, or the like.

The hole transport region HTR may also include a charge generating material to improve conductivity in addition to the above-mentioned materials. The charge generating material may be uniformly or non-uniformly dispersed in the hole transport region HTR. The charge generating material may be, e.g., a p-dopant. The p-dopant may be one of a quinone derivative, a metal oxide, and a compound containing a cyano group, but the disclosure is not limited thereto. For example, non-limiting examples of the p-dopant may include quinone derivatives such as TCNQ (tetracyanoquinodimethane) and F4-TCNQ (2,3,5,6-tetrafluoro-7,7',8,8'-tetracyanoquinodimethane); and metal oxides such as tungsten oxide and molybdenum oxide, but the disclosure is not limited thereto.

Each layer of the electron transport region ETR may be formed using a general method. For example, the electron transport region ETR may be formed by using a variety of methods such as vacuum deposition, spin coating, casting, a Langmuir-Blodgett (LB) technique, inkjet printing, laser printing, and laser induced thermal imaging (LITI).

The electron injection layer included in the electron transport region ETR may include an electron injection material. As the electron injection material, a metal halide such as LiF, NaCl, CsF, RbCl, or RbI, a lanthanide metal such as Yb or $Li_2O$, a metal oxide such as BaO, or lithium quinolate (LiQ) may be used, but the disclosure is not limited thereto. The electron injection layer may also be made of a material in which an electron transport material and an insulating organo metal salt are mixed. The organo metal salt may be a material having an energy band gap of about 4 eV or more. Specifically, for example, the organo metal salt may include metal acetate, metal benzoate, metal acetoacetate, metal acetylacetonate, or metal stearate.

However, the disclosure is not limited thereto, and the electron injection layer and the n-type charge generating layer n-CGL1 described with reference to FIG. 1 may include a same material.

The electron injection layer according to an embodiment may include a compound represented by Chemical Formula 1 below.

[Chemical Formula 1]

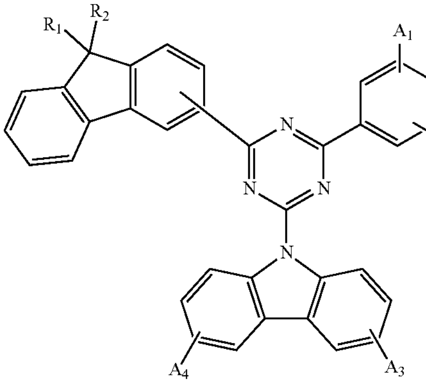

In Chemical Formula 1, each of $R_1$ and $R_2$ may independently include an aliphatic compound, an aromatic compound, or a hetero compound having 1 to 30 carbon atoms, and each of $A_1$, $A_2$, $A_3$, and $A_4$ may independently include hydrogen, an aliphatic compound, an aromatic compound, or a hetero compound, or an aliphatic compound, an aromatic compound, or a hetero compound each substituted with at least one of CN, F, or CF3.

The electron injection layer according to an embodiment may be formed of an organic compound represented by Chemical Formula 1 above. The electron injection layer may not include a separate inorganic material.

A value of a lowest unoccupied molecular orbital (LUMO) energy level of the electron injection layer according to an embodiment may be in a rage of about −2.8 eV to about −3.4 eV. For example, in Chemical Formula 1, $A_1$ and $A_2$ may each be a main component that determines the LUMO energy level value of the electron injection layer. In Chemical Formula 1, $A_1$ and $A_2$ may each be a substituent that attracts electrons. As the electron-attracting force of each of $A_1$ and $A_2$ increases, the LUMO energy level value of the electron injection layer may be lowered, and an absolute value of the LUMO energy level of the electron injection layer may be increased.

The compound represented by Chemical Formula 1 constituting the electron injection layer according to an embodiment may include a carbazole-based compound. The carbazole-based compound may increase a dipole moment of the compound expressed by Chemical Formula 1. As the dipole moment of the compound expressed by the Chemical Formula 1 increases, electrons may readily move through the electron injection layer. The dipole moment of the compound represented by the Chemical Formula 1 according to an embodiment may be about 2.0 debyes or more.

The compound represented by the Chemical Formula 1 constituting the electron injection layer according to an embodiment may include a triazine-based compound. Electron mobility of the electron injection layer may be improved by the triazine-based compound.

The compound represented by Chemical Formula 1 constituting the electron injection layer according to an embodiment may include a functional group having $R_1$ and $R_2$. The functional group having $R_1$ and $R_2$ may be relatively bulky, and the electron injection layer including the compound represented by Chemical Formula 1 may have an amorphous characteristic.

The electron injection layer according to an embodiment may be individually formed of an organic compound represented by Chemical Formula 1 above. Since the electron injection layer is made of a single compound, it may be formed using one deposition head. An electron injection layer including two or more compounds may be formed using an angle limiting plate for co-evaporation. However, since the electron injection layer according to an embodiment is formed using one deposition head, a manufacturing process may be simplified and a manufacturing cost may be reduced.

The compound represented by Chemical Formula 1 may be represented by following Chemical Formula 1-1 to Chemical Formula 1-4.

[Chemical Formula 1-1]

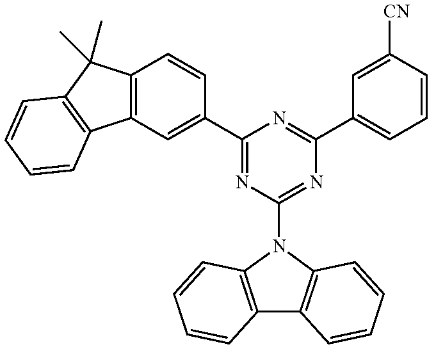

[Chemical Formula 1-2]

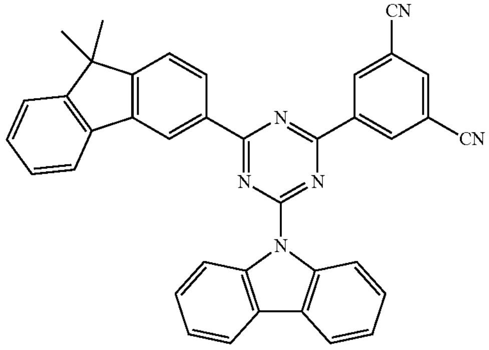

-continued

[Chemical Formula 1-3]

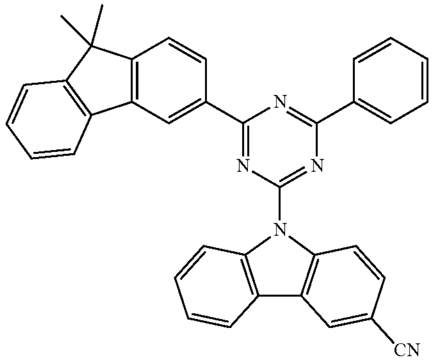

[Chemical Formula 1-4]

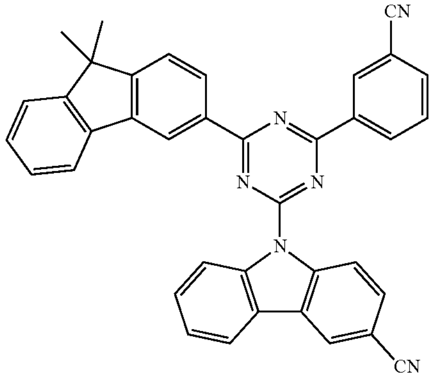

The electron injection layer according to an embodiment may not include an inorganic material. In the case of the electron injection layer formed by doping an inorganic material, a leakage current may flow to an adjacent light-emitting device in a horizontal direction. Accordingly, color mixture may be caused by emitting light on other light-emitting devices where no voltage is applied. Since the electron injection layer according to an embodiment does not include an inorganic material, it may be possible to control a current leakage and unintentional light emission of the light-emitting device. A light-emitting device including an electron injection layer according to an embodiment and a display panel including the same may improve display quality without color mixing.

The electron transport layer included in the electron transport region ETR may include an electron transport material. The electron transport material may include a triazine-based compound or an anthracene-based compound. However, the disclosure is not limited thereto, and the electron transport material may include, e.g., $Alq_3$ (tris(8-hydroxyquinolinato)aluminum), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, TPBi (1,3,5-tris(1-phenyl-1H-benzo[d]imidazol-2-yl)benzene), BCP (2,9-dimethyl-4,7-diphenyl-1,10-phenanthroline), Bphen (4,7-diphenyl-1,10-phenanthroline), TAZ (3-(4-biphenylyl)-4-phenyl-5-tert-butylphenyl-1,2,4-triazole), NTAZ (4-(naphthalen-1-yl)-3,5-diphenyl-4H-1,2,4-triazole), tBu-PBD (2-(4-biphenylyl)-5-(4-tert-butylphenyl)-1,3,4-oxadiazole), BAlq (bis(2-methyl-8-quinolinolato-N1,O8)-(1,1'-biphenyl-4-olato)aluminum), $Bebq_2$ (berylliumbis(benzoquinolin-10-olate), ADN (9,10-di(naphthalene-2-yl)anthracene), TSPO1 (diphenyl(4-(triphenylsilyl)phenyl)phosphine oxide), TPM-TAZ (2,4,6-tris(3-(pyrimidin-5-yl)phenyl)-1,3,5-triazine), and a mixture thereof.

Each of the electron injection layers may have a thickness of about 1 Å to about 500 Å, or about 3 Å to about 300 Å. In case that the thickness of the electron injection layer satisfies the range as described above, a satisfactory electron injection characteristic may be obtained without a substantial increase in driving voltage.

Each of the electron transport layers may have a thickness of about 100 Å to about 1000 Å, e.g., about 150 Å to about 500 Å. In case that the thickness of the electron transport layer satisfies the range as described above, a satisfactory electron transport characteristic may be obtained without a substantial increase in driving voltage.

The hole blocking layer may be a layer serving to prevent leakage of holes from the hole transport region HTR to the electron transport region ETR. A thickness of the hole blocking layer may be about 10 Å to about 1000 Å.

The hole blocking layer may include at least one of, e.g., BCP (2,9-dimethyl-4,7-diphenyl-1,10-phenanthroline), Bphen (4,7-diphenyl-1,10-phenanthroline), and T2T (2,4,6-tri([1,1'-biphenyl]-3-yl)-1,3,5-triazine), but the disclosure is not limited thereto.

Each of the emission parts EL may include a light emitting layer EML. Specifically, each emission part EL may include one emission layer EML. Multiple emission layers EML may emit light of different colors or may emit light of a same color. According to an embodiment, the first and second emission layers EML1 and EML2 included in the first and second emission parts EL1 and EL2 may emit blue light, but the disclosure is not limited thereto.

The emission layer EML may include at least one selected from an organic compound and a semiconductor compound, but the disclosure is not limited thereto. In case that the emission layer EML includes an organic compound, the light-emitting device may be referred to as an organic emission element.

The organic compound may contain a host and a dopant. The semiconductor compound may be a quantum dot, for example, the light-emitting device may be a quantum dot light-emitting device. As another example, the semiconductor compound may be an organic and/or inorganic perovskite.

A thickness of the emission layer EML may be about 0.1 nm to about 100 nm. Specifically, the thickness of the emission layer EML may be about 15 nm to about 50 nm. More specifically, in case that the emission layer EML emits blue light, a thickness of the blue emission layer may be about 15 nm to about 20 nm, in case that the emission layer emits green light, a thickness of the green emission layer may be about 20 nm to about 40 nm, and in case that the emission layer emits red light, a thickness of the red emission layer may be about 40 nm to about 50 nm. In case that the above-described range is satisfied, the light-emitting device may exhibit an excellent light emitting characteristic without a substantial increase in driving voltage.

The emission layer EML may include a host material and a dopant material. The emission layer EML may be formed by using a phosphorescent or fluorescent emission material as a dopant in the host material. The emission layer EML may be formed by including a thermally activated delayed fluorescence (TADF) dopant in the host material. As another example, the emission layer EML may include a quantum dot material as an emission material. A core of the quantum dot may be selected from a group of II-VI compound, a group III-V compound, a group IV-VI compound, a group IV element, a group IV compound, and a combination thereof.

The color of light emitted from the emission layer EML may be determined by a combination of a host material and a dopant material, or a type of a quantum dot material and a size of a core.

As the host material of the emission layer EML, a known material may be used and may not be particularly limited, but may be selected from among a fluoranthene derivative, a pyrene derivative, an arylacetylene derivative, an anthracene derivative, a fluorene derivative, a perylene derivative, a chrysene derivative, and the like. The pyrene derivative, the perylene derivative, and the anthracene derivative may be selected.

As the dopant material of the emission layer EML, a known material may be used, and although not particularly limited, a styryl derivative (e.g., 1,4-bis[2-(3-N-ethylcarbazoryl)vinyl]benzene (BCzVB), 4-(di-p-tolylamino)-4'-[(di-p-tolylamino)styryl]stilbene (DPAVB), N-(4-((E)-2-(6-((E)-4-(diphenylamino)styryl)naphthalen-2-yl)vinyl)phenyl)-N-phenylbenzenamine (N-BDAVBi), perylene and its derivatives (e.g., 2,5,8,11-tetra-t-butylperylene (TBP)), pyrene and its derivatives (e.g., 1,1-dipyrene, 1,4-dipyrenylbenzene, 1,4-bis(N,N-diphenylamino)pyrene), N1,N6-di (naphthalen-2-yl)-N1, N6-diphenylpyrene-1,6-diamine), and the like may be used.

The light-emitting device may further include a capping layer CPL disposed on the second electrode E2. The capping layer CPL may include, e.g., α-NPD, NPB, TPD, m-MTDATA, $Alq_3$, CuPc, TPD15 (N4,N4,N4',N4'-tetra(biphenyl-4-yl)biphenyl-4,4'-diamine), TCTA (4,4',4"-tris(N-carbazolyl)triphenylamine), N,N'-bis(naphthalen-1-yl), etc. The capping layer CPL may serve to help light emitted from the emission layer EML of the light-emitting device to be efficiently emitted to the outside of the light-emitting device. In case that the light-emitting device of an embodiment also includes a thin film encapsulation layer, the capping layer CPL may be disposed between the second electrode E2 and the thin film encapsulation layer.

Figure 3:
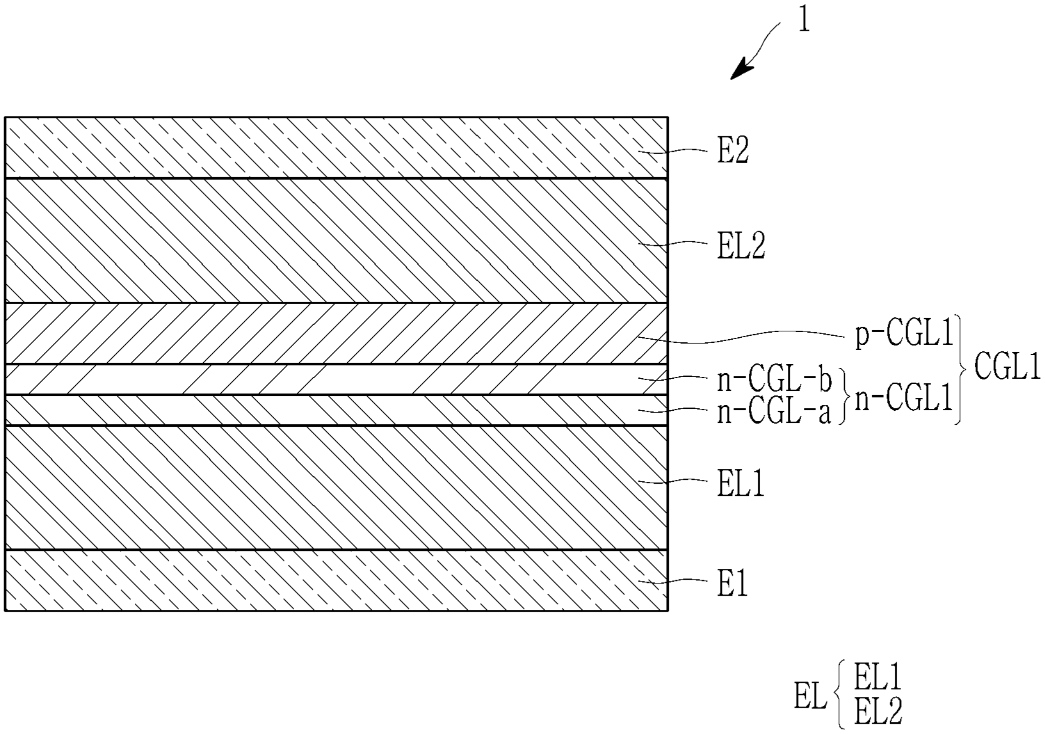
FIG. 3 illustrates a schematic cross-sectional view of a light-emitting device according to an embodiment.
Figure 4:
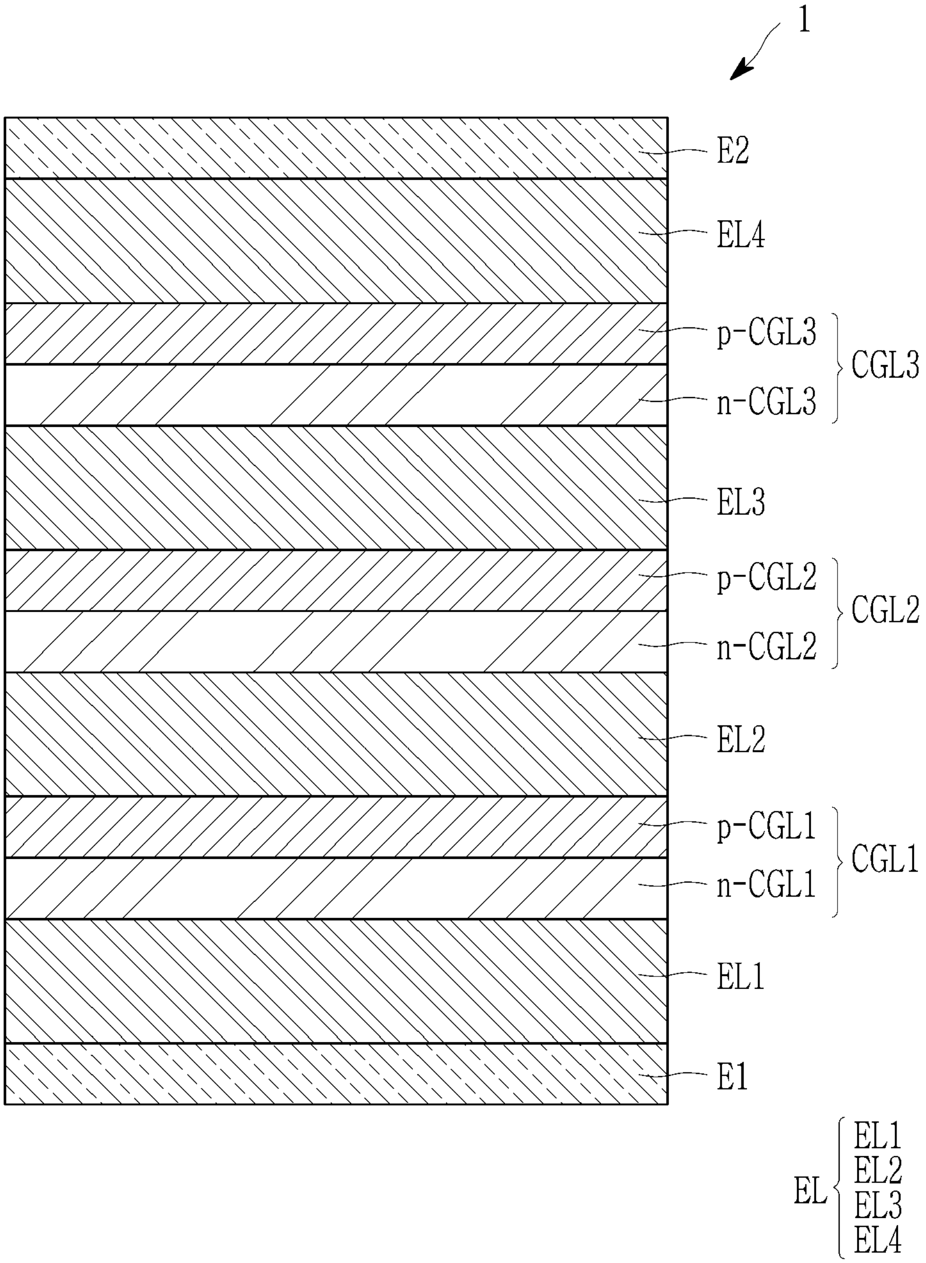
FIG. 4 illustrates a schematic cross-sectional view of a light-emitting device according to an embodiment.

Hereinafter, a light-emitting device according to an embodiment will be described with reference to FIG. 3 and FIG. 4. FIG. 3 and FIG. 4 each illustrates a schematic cross-sectional view of a light-emitting device according to an embodiment. A description of the same or similar continent elements as those described above will be omitted.

First, referring to FIG. 3, the n-type charge generating layer n-CGL1 according to an embodiment may include at least two or more sub n-type charge generating layers. The specification has illustrated and described an embodiment including a first sub n-type charge generating layer n-CGL-a and a second sub n-type charge generating layer n-CGL-b, but the disclosure is not limited thereto.

The first sub n-type charge generating layer n-CGL-a may be positioned adjacent to the first emission part EL1, and the second sub n-type charge generating layer n-CGL-b may be positioned adjacent to the second emission part EL2. A LUMO energy level of the first sub n-type charge generating layer n-CGL-a may be greater than a LUMO energy level of the second sub n-type charge generating layer n-CGL-b. An absolute value of the LUMO energy level of the second sub n-type charge generating layer n-CGL-b may be greater than an absolute value of the LUMO energy level of the first sub n-type charge generating layer n-CGL-a. The second sub n-type charge generating layer n-CGL-b may be disposed adjacent to the p-type charge generating layer p-CGL1, so that electrons may be readily transferred from the p-type charge generating layer p-CGL1 to the n-type charge generating layer n-CGL1.

Referring to FIG. 4, in case that the light-emitting device 1 includes m emission parts EL, the light-emitting device 1 may include (m−1) charge generating layers CGL1, CGL2, and CGL3 provided between the adjacent emission parts EL. The light emitting device 1 according to an embodiment may include a first charge generating layer CGL1 positioned between the first emission part EL1 and the second emission part EL2, a second charge generating layer CGL2 positioned between the second emission part EL2 and the third emission part EL3, and a third charge generating layer CGL3 positioned between the third emission part EL3 and the fourth emission part EL4. Although the specification shows the embodiment including three charge generating layers CGL1, CGL2, and CGL3, the disclosure is not limited thereto, and may vary depending on the number of emission parts EL.

Each of the charge generating layers CGL1, CGL2, and CGL1 may include n-type charge generating layers n-CGL1, n-CGL2, and n-CGL3 that provide electrons to the emission part EL, and p-type charge generating layers p-CGL1, p-CGL2, and p-CGL3 that provide holes to the emission part EL. Although not illustrated, a buffer layer may be also disposed between the n-type charge generating layers n-CGL1, n-CGL2, and n-CGL3 and the p-type charge generating layers p-CGL1, p-CGL2, and p-CGL3 according to an embodiment.

The first charge generating layer CGL1 may include a first (-n) type charge generating layer n-CGL1 and a first (-p) type charge generating layer p-CGL1. The first (-n) type charge generating layer n-CGL1 may be disposed adjacent to the first emission part EL1, and the first (-p) type charge generating layer p-CGL1 may be disposed adjacent to the second emission part EL2. The second charge generating layer CGL2 may include a second (-n) type charge generating layer n-CGL2 and a second (-p) type charge generating layer p-CGL2. The second (-n) type charge generating layer n-CGL2 may be disposed adjacent to the first emission part EL2, and the second (-p) type charge generating layer p-CGL2 may be disposed adjacent to the third emission part EL3. The third charge generating layer CGL3 may include a third (-n) type charge generating layer n-CGL3 and a third (-p) type charge generating layer p-CGL3. The third (-n) type charge generating layer n-CGL3 may be disposed adjacent to the first emission part EL3, and the third (-p) type charge generating layer p-CGL3 may be disposed adjacent to the third emission part EL4.

At least one of the first (-n) type charge generating layer n-CGL1, the second (-n) type charge generating layer n-CGL2, and the third (-n) type charge generating layer n-CGL3 may include a same material as the n-type charge generating layer described with reference to FIG. 1.

Figure 5:
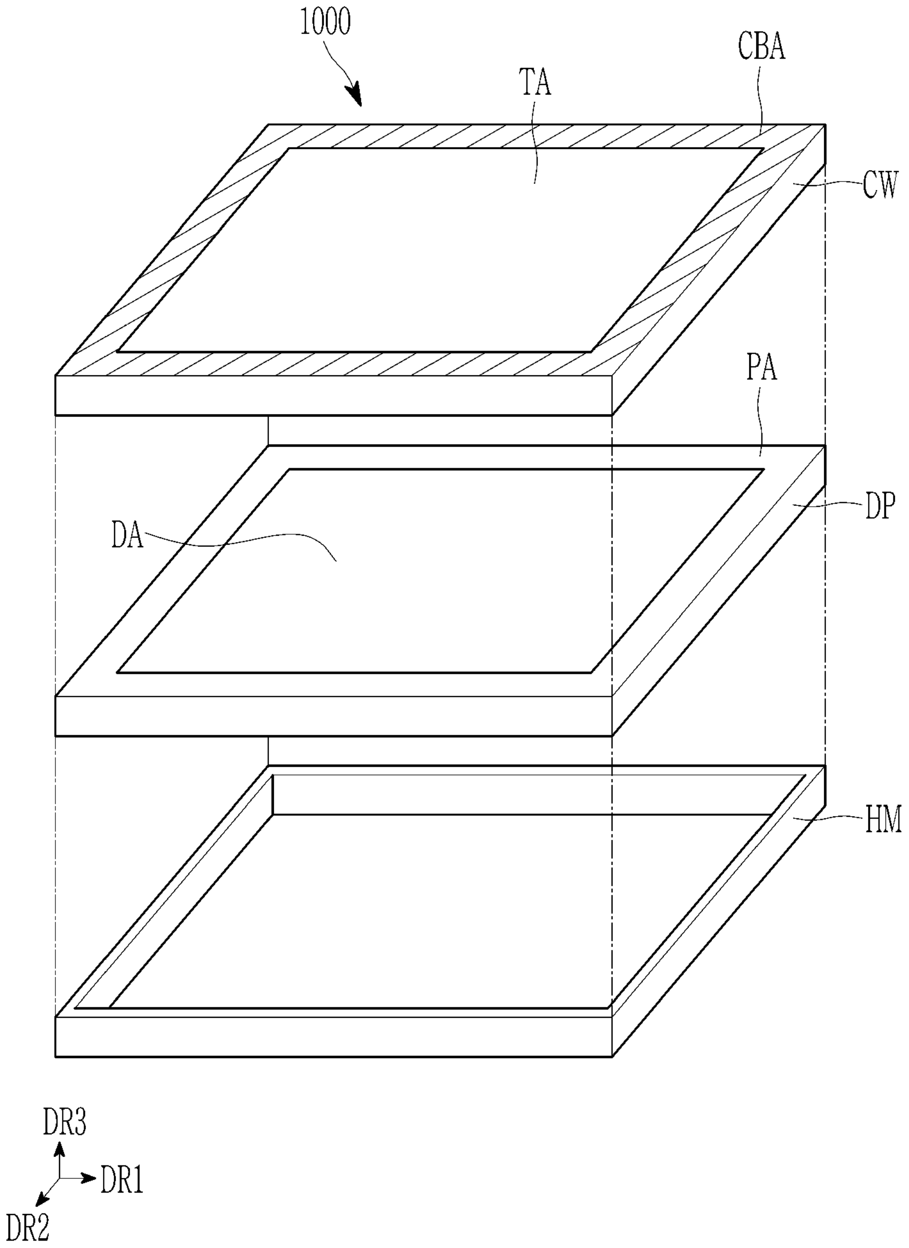
FIG. 5 illustrates a schematic exploded perspective view of a display device according to an embodiment.

A display device according to an embodiment will now be described with reference to FIG. 5. FIG. 5 illustrates a schematic exploded perspective view of a display device according to an embodiment.

Referring to FIG. 5, a display device according to an embodiment may include a cover window CW, a display panel DP, and a housing HM.

The cover window CW may include an insulating panel. For example, the cover window CW may be formed of glass, plastic, or a combination thereof.

A front surface of the cover window CW may define a front surface of the display device 1000. A transmissive area TA may be an optically transparent area. For example, the transmissive area TA may be an area having visible ray transmittance of about 90% or more.

A blocking area CBA may define a shape of the transmissive area TA. The blocking area CBA may be disposed adjacent to the transmissive area TA to surround the transmissive area TA. The blocking area CBA may be an area having relatively low light transmittance compared to the transmissive area TA. The blocking area CBA may include an opaque material that blocks light. The blocking area CBA may have a color. The blocking area CBA may be defined by a bezel layer provided separately from a transparent substrate defining the transmissive area TA, or may be defined by an ink layer formed by being inserted or colored in a transparent substrate.

In the display panel DP, a front (or top) surface on which an image is displayed may be parallel to a surface defined by a first direction DR1 and a second direction DR2. A direction normal to a surface on which an image is displayed, i.e., a thickness direction of the display panel DP, may be represented as a third direction DR3. A front (or top) surface and a back (or bottom) surface of each of the members may be separated in the third direction DR3. However, the directions indicated by the first to third directions DR1, DR2, and DR3 may be converted to other directions as a relative concept.

The display panel DP may be a flat rigid display panel, but the disclosure is not limited thereto, and may also be a flexible display panel. The display panel DP may be formed as an organic light emitting panel. However, a type of the display panel DP is not limited thereto, and it may be formed as various types of panels. For example, the display panel DP may be formed as a liquid crystal display panel, an electrophoretic display panel, an electrowetting display panel, or the like. The display panel DP may be formed as a next-generation display panel such as a micro light emitting diode (micro LED) display panel, a quantum dot light emitting diode display panel, or a quantum dot organic light emitting diode display panel.

The micro LED display panel may be formed in such a way that a light emitting diode having a size of 10 to 100 μm constitutes each pixel. Such a micro light emitting diode display panel may use an inorganic material, may omit a backlight, may have a fast reaction speed, may implement high luminance with low power, and may not be broken in case of bending. A quantum dot light emitting diode display panel may be formed by attaching a film containing quantum dots or using a material containing quantum dots. Quantum dots may refer to particles made of an inorganic material such as indium or cadmium, emitting light by themselves, and having a diameter of several nanometers or less. Light of a desired color may be displayed by controlling a particle size of the quantum dots. The quantum dot organic light emitting diode display panel may be formed by a method of realizing color by using a blue organic light emitting diode as a light source and attaching a film containing red and green quantum dots thereon, or depositing a material containing red and green quantum dots. The display panel DP according to an embodiment may be formed as various other display panels.

As illustrated FIG. 5, the display panel DP may include a display area DA in which an image is displayed, and a non-display area PA adjacent to the display area DA. The non-display area PA may be an area in which an image is not displayed. The display area DA may have a rectangular shape, for example, and the non-display area PA may have a shape surrounding the display area DA. However, the disclosure is not limited thereto, and shapes of the display area DA and the non-display area PA may be relatively designed.

The housing HM may provide an inner space. The display panel DP may be mounted inside of the housing HM. In addition to the display panel DP, various electronic components, for example, a power supply part, a storage device, and an audio input/output module, may be mounted inside of the housing HM.

Figure 6:
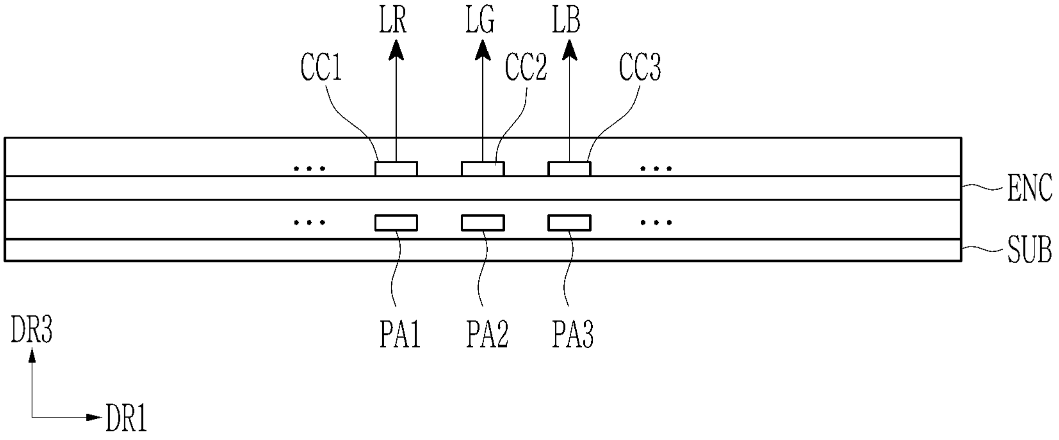
FIG. 6 illustrates a schematic cross-sectional view of a display panel according to an embodiment.
Figure 7:
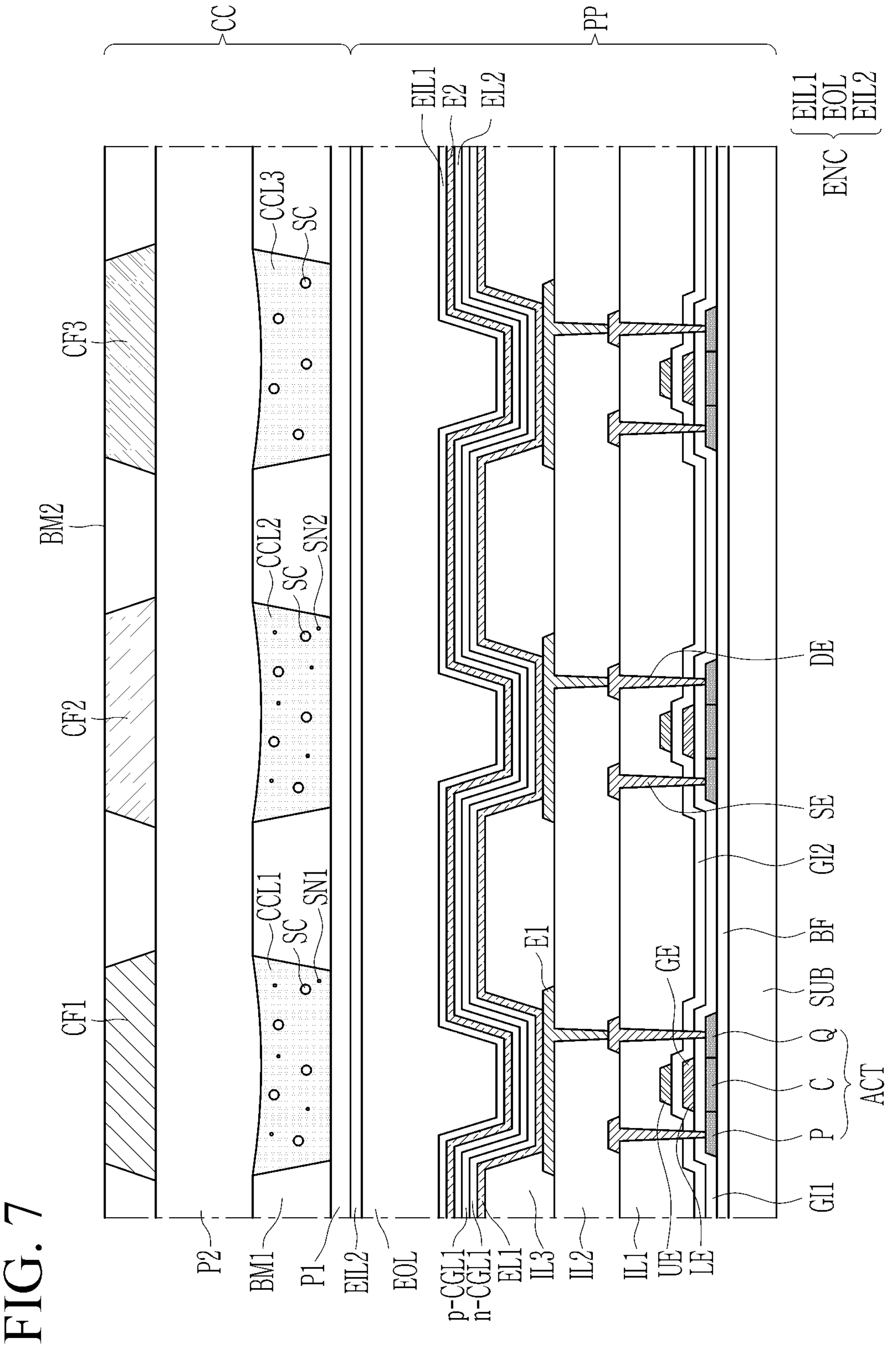
FIG. 7 illustrates a schematic cross-sectional view of a display panel according to an embodiment.

Hereinafter, a display area of a display panel according to an embodiment will be described with reference to FIG. 6 and FIG. 7. FIG. 6 illustrates a schematic cross-sectional view of a display panel according to an embodiment, and FIG. 7 illustrates a schematic cross-sectional view of a display panel according to an embodiment.

First, referring to FIG. 6, multiple pixels PA1, PA2, and PA3 may be formed on a substrate SUB corresponding to the display area DA. Each of the pixels PA1, PA2, and PA3 may include multiple transistors and a light-emitting device electrically connected thereto.

An encapsulation layer ENC may be disposed on the pixels PA1, PA2, and PA3. The display area DA may be protected from external air or moisture by the encapsulation layer ENC. The encapsulation layer ENC may be integrally provided to overlap an entire surface of the display area DA, and may be partially disposed on the non-display area PA.

A first color conversion unit CC1, a second color conversion unit CC2, and a transmission unit CC3 may be positioned on the encapsulation layer ENC. The first color conversion unit CC1 may overlap the first pixel PA1, the second color conversion unit CC2 may overlap the second pixel PA2, and the transmissive unit CC3 may overlap the third pixel PA3.

Light emitted from the first pixel PA1 may pass through the first color conversion unit CC1 to provide red light LR. Light emitted from the second pixel PA2 may pass through the second color conversion unit CC2 to provide green light LG. The light emitted from the third pixel PA3 may pass through the transmissive unit CC3 to provide blue light LB.

Hereinafter, a stacked structure of each of the pixels PA1, PA2, and PA3 and a stacked structure of each of the color conversion units CC1 and CC2 and the transmissive unit CC3 will be described.

Referring to FIG. 7, a color conversion unit CC may be positioned on a pixel portion PP including the first to third pixels PA1, PA2, and PA3. Referring to FIG. 7, the pixel portion PP according to an embodiment may include a substrate SUB.

The substrate SUB may include an inorganic insulating material such as glass, or an organic insulating material such as plastic, e.g., polyimide (PI). The substrate SUB may be a single layer or a multilayer. The substrate SUB may have a structure in which at least one base layer including a polymer resin and an inorganic layer are alternately stacked.

The substrate SUB may have various degrees of flexibility. The substrate SUB may be a rigid substrate or a flexible substrate capable of bending, folding, rolling, or the like.

A buffer layer BF may be disposed on the substrate SUB. The buffer layer BF may prevent impurities from being transferred from the substrate SUB to an upper layer of the buffer layer BF, particularly a semiconductor layer ACT, thereby preventing deterioration of a characteristic of the semiconductor layer ACT and reducing stress. The buffer layer BF may include an inorganic insulating material such as a silicon nitride or a silicon oxide, or may include an organic insulating material. A portion or an entire portion of the buffer layer BF may be omitted.

The semiconductor layer ACT may be disposed on the buffer layer BF or on the substrate SUB. The semiconductor layer ACT may include at least one of polysilicon and an oxide semiconductor. The semiconductor layer ACT may include a channel region C, a first region P, and a second region Q. The first region P and the second region Q are disposed at opposite sides of the channel region C, respectively. The channel region C may be doped with a smaller amount of impurities or may be a semiconductor that is not doped with impurities, and the first region P and the second region Q may include a semiconductor doped with a larger amount of impurities compared to the channel region C. The semiconductor layer ACT may be formed by using an oxide semiconductor, and a separate protective layer (not illustrated) may be added to protect an oxide semiconductor material that is vulnerable to external environments such as a high temperature.

A first gate insulating layer GI1 may be disposed on the semiconductor layer ACT.

A gate electrode GE and a lower electrode LE are positioned on the first gate insulating layer GI1. According to an embodiment, the gate electrode GE and the lower electrode LE may be integral each other. The gate electrode GE and the lower electrode LE may be a single layer or a multilayer in which a metal film including any one of copper (Cu), a copper alloy, aluminum (Al), an aluminum alloy, molybdenum (Mo), a molybdenum alloy, titanium (Ti), and a titanium alloy is stacked. The gate electrode GE may overlap the channel region C of the semiconductor layer ACT.

The second gate insulating layer GI2 may be positioned on the gate electrode GE and the first gate insulating layer GI1. The first gate insulating layer GI1 and the second gate insulating layer GI2 may be a single layer or multiple layers including at least one of a silicon oxide ($SiO_x$), a silicon nitride ($SiN_x$), and a silicon oxynitride ($SiO_xN_y$).

An upper electrode UE may be positioned on the second gate insulating layer GI2. The upper electrode UE may form a storage capacitor while overlapping the lower electrode LE.

A first interlayer insulating layer IL1 may be disposed on the upper electrode UE. The first interlayer insulating layer IL1 may be a single layer or multiple layers including at least one of a silicon oxide ($SiO_x$), a silicon nitride ($SiN_x$), and a silicon oxynitride ($SiO_xN_y$).

A source electrode SE and a drain electrode DE may be positioned on the first interlayer insulating layer IL1. The source electrode SE and the drain electrode DE may be respectively electrically connected to the first region P and the second region Q of the semiconductor layer ACT through contact holes formed in the first interlayer insulating layers.

The source electrode SE and the drain electrode DE may include aluminum (Al), silver (Ag), magnesium (Mg), gold (Au), nickel (Ni), chromium (Cr), nickel (Ni), calcium (Ca), molybdenum (Mo), titanium (Ti), tungsten (W), copper (Cu), and/or the like, and may have a single layer structure or a multilayer structure including the material.

A first interlayer insulating layer IL1 and a second interlayer insulating layer IL2 may be positioned on the source electrode SE and the drain electrode DE. The second interlayer insulating layer IL2 may include a general purpose polymer such as poly(methyl methacrylate) (PMMA) or polystyrene (PS), a polymer derivative having a phenolic group, an organic insulating material such as an acrylic polymer, an imide polymer, a polyimide, an acrylic polymer, a siloxane polymer, etc.

A first electrode E1 may be disposed on the second interlayer insulating layer IL2. The first electrode E1 may be electrically connected to the drain electrode DE through a contact hole in the second interlayer insulating layer IL2.

The first electrode E1 may include a metal such as silver (Ag), lithium (Li), calcium (Ca), aluminum (Al), magnesium (Mg), and gold (Au), and may also include a transparent conductive oxide (TCO) such as an indium zinc oxide (IZO) and an indium tin oxide (ITO). The first electrode E1 may be formed as a single layer including a metal material or a transparent conductive oxide, or a multiple layer including the same. For example, the first electrode E1 may have a triple layer structure of indium tin oxide (ITO)/silver (Ag)/indium tin oxide (ITO).

A transistor including the gate electrode GE, the semiconductor layer ACT, the source electrode SE, and the drain electrode DE may be electrically connected to the first electrode E1 to supply a current to a light emitting element.

A partition wall or bank IL3 may be positioned on the second interlayer insulating layer IL2 and the first electrode E1. Although not illustrated, a spacer may be positioned on the bank IL3. The bank IL3 may overlap at least a portion of the first electrode E1, and may have an opening defining an emission area.

The bank IL3 may include a general purpose polymer such as poly(methyl methacrylate) (PMMA) or polystyrene (PS), a polymer derivative having a phenolic group, an organic insulating material such as an acrylic polymer, an imide polymer, a polyimide, an acrylic polymer, a siloxane polymer, etc.

A first emission part EL1, an n-type charge generating layer n-CGL1, a p-type charge generating layer p-CGL1, and a second emission part EL2 may be sequentially positioned on the bank IL3. The first emission part EL1, the n-type charge generating layer n-CGL1, the p-type charge generating layer p-CGL1, and the second emission part EL2 may be commonly disposed over multiple pixels. However, the disclosure is not limited thereto, and at least a portion of the first emission part EL1, the n-type charge generating layer n-CGL1, the p-type charge generating layer p-CGL1, and the second emission part EL2 may be patterned to be positioned only in the opening of the bank IL3. A description of the light-emitting device according to an embodiment described above with reference to FIG. 1 to FIG. 3 may be applied for detailed descriptions of the light-emitting device according to an embodiment.

The second electrode E2 may be positioned on the second emission part of EL2. The second electrode E2 may include a reflective metal including calcium (Ca), barium (Ba), magnesium (Mg), aluminum (Al), silver (Ag), gold (Au), nickel (Ni), chromium (Cr), lithium (Li), calcium (Ca), etc., or a transparent conductive oxide (TCO) such as an indium tin oxide (ITO) or an indium zinc oxide (IZO).

The first electrode E1, the first emission part EL1, the n-type charge generating layer n-CGL1, the p-type charge generating layer p-CGL1, the second emission part EL2, and the second electrode E2 may constitute a light-emitting device. Herein, the first electrode E1 may be an anode which is a hole injection electrode, and the second electrode E2 may be a cathode which is an electron injection electrode. However, the disclosure is not limited thereto, and the first electrode E1 may be a cathode and the second electrode E2 may be an anode depending on a driving method of a light emitting device.

An encapsulation layer ENC may be disposed on the second electrode E2. The encapsulation layer ENC may cover and seal not only the upper surface of the light emitting element but also the side surfaces. Since the light emitting element is very vulnerable to moisture and oxygen, the encapsulation layer ENC may seal the light emitting element to block inflow of moisture and oxygen from the outside.

The encapsulation layer ENC may include multiple layers, and among them, may be formed of a composite film including both an inorganic layer and an organic layer, for example, the encapsulation layer ENC may be formed as a triple layer in which a first inorganic encapsulation layer EIL1, an encapsulation organic layer EOL, and a second inorganic encapsulation layer EIL2 are sequentially formed.

The first encapsulation inorganic layer EIL1 may cover the second electrode E2. The first encapsulation inorganic layer EIL1 may prevent external moisture or oxygen from penetrating into the light emitting element. For example, the first encapsulation inorganic layer EIL1 may include a silicon nitride, a silicon oxide, a silicon oxynitride, or a combination thereof. The first encapsulation inorganic layer EIL1 may be formed through a deposition process.

The encapsulation organic layer EOL may be disposed on the first encapsulation inorganic layer EIL1 to contact the first encapsulation inorganic layer EIL1. Curves formed on an upper surface of the first encapsulation inorganic layer EIL1 or particles present on the first encapsulation inorganic layer EIL1 may be covered by the encapsulation organic layer EOL to block an influence of a surface state of the upper surface of the first encapsulation inorganic layer EIL1 on the components formed on the encapsulation organic layer EOL. The encapsulation organic layer EOL may relieve stress between the layers that are in contact therewith. The encapsulation organic layer EOL may include an organic material, and may be formed through a solution process such as spin coating, slit coating, or an inkjet process.

The second encapsulation inorganic layer EIL2 may be disposed on the encapsulation organic layer EOL to cover the encapsulation organic layer EOL. The second encapsulation inorganic layer EIL2 may be stably formed on a relatively flat surface compared to that of the first encapsulation inorganic layer EIL1. The second encapsulation inorganic layer EIL2 may encapsulate moisture, etc. emitted from the encapsulation organic layer EOL, to prevent it from being introduced from the outside. The second encapsulation inorganic layer EIL2 may include a silicon nitride, a silicon oxide, a silicon oxynitride, or a combination thereof. The second encapsulation inorganic layer EIL2 may be formed through a deposition process.

Although not illustrated in this specification, a capping layer positioned between the second electrode E2 and the encapsulation layer ENC may be also included. The capping layer may include an organic material. The capping layer may protect the second electrode E2 from a subsequent process, e.g., a sputtering process, and may improve light output efficiency of the light emitting element. The capping layer may have a refractive index that is greater than that of the first encapsulation inorganic layer EIL1.

The color conversion unit CC may be positioned on the encapsulation layer ENC.

The color conversion unit CC may include a first insulating layer P1 positioned on the encapsulation layer ENC. The first insulating layer P1 may be integrally formed to overlap the entire display area. The first insulating layer P1 may be a single layer or multiple layers including at least one of a silicon oxide ($SiO_x$), a silicon nitride ($SiN_x$), and a silicon oxynitride ($SiO_xN_y$).

A first light blocking layer BM1 may be positioned on the first insulating layer P1. The first light blocking layer BM1 may define a region in which a first color conversion layer CCL1, a second color conversion layer CCL2, and a transmissive layer CCL3 are positioned.

The first color conversion layer CCL1, the second color conversion layer CCL2, and the transmissive layer CCL3 may be positioned in the region defined by the first light blocking layer BM1. The first color conversion layer CCL1, the second color conversion layer CCL2, and the transmissive layer CCL3 may be formed by an inkjet process, but the disclosure is not limited thereto, and may be formed by using another manufacturing method.

The transmissive layer CCL3 may transmit light of a first wavelength incident from the light-emitting device, and may include multiple scatterers SC. Light of a first wavelength may be blue light having a maximum emission peak wavelength of about 380 nm to about 480 nm, e.g., about 420 nm or more, about 430 nm or more, about 440 nm or more, or about 445 nm or more, and about 470 nm or less, about 460 nm or less, or about 455 nm or less.

The first color conversion layer CCL1 may color-convert light of the first wavelength incident from the light-emitting device into red light, and may include the multiple scatterers SC and multiple first quantum dots SN1. A maximum emission peak wavelength of red light may be in a range of about 600 nm to about 650 nm, e.g., about 620 nm to about 650 nm.

The second color conversion layer CCL2 may color-convert light of the first wavelength incident from the light-emitting device into green light, and may include the multiple scatterers SC and multiple second quantum dots SN2. The green light may have a maximum emission peak wavelength of about 500 nm to about 550 nm, e.g., about 510 nm to about 550 nm.

The scatterers SC may increase light efficiency by scattering light incident onto the first color conversion layer CCL1, the second color conversion layer CCL2, and the transmissive layer CCL3.

Each of the first quantum dots SN1 and the second quantum dots SN2 (hereinafter, also referred to as semiconductor nanocrystals) may independently include a Group II-VI compound, a Group III-V compound, a Group IV-VI compound, a Group IV element or compound, a Group I-III-VI compound, a Group II-III-VI compound, a Group I-II-IV-VI compound, or a combination thereof. The quantum dots may not contain cadmium.

The Group II-VI compound may be a two-element compound selected from CdSe, CdTe, ZnS, ZnSe, ZnTe, ZnO, HgS, HgSe, HgTe, MgSe, MgS, and a mixture thereof; a three-element compound selected from AgInS, CuInS, CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, and a mixture thereof; or a four-element compound selected from HgZnTeS, CdZnSeS, CdZnSeTe, CdZnSTe, CdHgSeS, CdHgSeTe, CdHgSTe, HgZnSeS, HgZnSeTe, HgZnSTe, and a mixture thereof. The Group II-VI compound may further include a Group III metal.

The Group III-V compound may be a two-element compound selected from GaN, GaP, GaAs, GaSb, AlN, AlP, AlAs, AlSb, InN, InP, InAs, InSb, and a mixture thereof; a three-element compound selected from GaNP, GaNAs, GaNSb, GaPAs, GaPSb, AlNP, AlNAs, AlNSb, AlPAs, AlPSb, InGaP, InNP, InNAs, InNSb, InPAs, InZnP, InPSb, and a mixture thereof; or a four-element compound selected from GaAlNP, GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, InAlPSb, InZnP, and a mixture thereof. The Group III-V compound may further include a Group II metal (e.g., InZnP).

The Group IV-VI compound may be a two-element compound selected from SnS, SnSe, SnTe, PbS, PbSe, PbTe, and a mixture thereof; a three-element compound selected from SnSeS, SnSeTe, SnSTe, PbSeS, PbSeTe, PbSTe, SnPbS, SnPbSe, SnPbTe, and a mixture thereof; or a four-element compound selected from SnPbSSe, SnPbSeTe, SnPbSTe, and a mixture thereof.

The Group IV element or compound may be a one-element compound selected from Si, Ge, and a combination thereof; or a two-element compound selected from SiC, SiGe, and a combination thereof, but embodiments are not limited thereto.

Examples of the Group 1-III-VI compound may include $CuInSe_2$, $CuInS_2$, CuInGaSe, and CuInGaS. Examples of the Group I-II-IV-VI compound may include, but are not limited to, CuZnSnSe and CuZnSnS. The Group IV element or compound may be a one-element compound selected from Si, Ge, and a mixture thereof; or a two-element compound selected from SiC, SiGe, and a mixture thereof.

The Group II-III-VI compound may be ZnGaS, ZnAlS, ZnInS, ZnGaSe, ZnAlSe, ZnInSe, ZnGaTe, ZnAlTe, ZnInTe, ZnGaO, ZnAlO, ZnInO, HgGaS, HgAlS, HgInS, HgGaSe, HgAlSe, HgInSe, HgGaTe, HgAlTe, HgInTe, MgGaS, MgAlS, MgInS, MgGaSe, MgAlSe, MgInSe, or a combination thereof, but embodiments are not limited thereto.

The Group I-II-IV-VI compound may be CuZnSnSe or CuZnSnS, but embodiments are not limited thereto.

In an embodiment, the quantum dots may not contain cadmium. The quantum dots may include semiconductor nanocrystals based on Group III-V compounds including indium and phosphorus. The Group III-V compound may further include zinc. The quantum dots may include semiconductor nanocrystals based on a Group II-VI compound including a chalcogen element (e.g., sulfur, selenium, tellurium, or a combination thereof) and zinc.

In the quantum dots, the two-element compound, the three-element compound, and/or the four-element compound described above may be present in particles at uniform concentrations, or they may be divided into states having partially different concentrations to be present in the same particle, respectively. A core/shell structure in which some quantum dots surround some other quantum dots may be possible. An interface between the core and the shell may have a concentration gradient in which a concentration of elements of the shell decreases closer to a center thereof.

In some embodiments, the quantum dot may have a core-shell structure that includes a core including the nanocrystal described above and a shell surrounding the core. The shell of the quantum dot may serve as a passivation layer for maintaining a semiconductor characteristic and/or as a charging layer for applying an electrophoretic characteristic to the quantum dot by preventing chemical denaturation of the core. The shell may be a single layer or a multilayer. An interface between the core and the shell may have a concentration gradient in which a concentration of elements of the shell decreases closer to a center thereof. An example of the shell of the quantum dot may include a metal or nonmetal oxide, a semiconductor compound, or a combination thereof.

Examples of an oxide of the metal or non-metal may include a two-element compound such as $SiO_2$, $Al_2O_3$, $TiO_2$, ZnO, MnO, $Mn_2O_3$, $Mn_3O_4$, CuO, FeO, $Fe_2O_3$, $Fe_3O_4$, CoO, $CO_3O_4$, NiO, and the like, or a three-element compound such as $MgAl_2O_4$, $CoFe_2O_4$, $NiFe_2O_4$, $CoMn_2O_4$, and the like, but embodiments are not limited thereto.

Examples of the semiconductor compound may include CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, AlSb, or the like, but embodiments are not limited thereto.

An interface between the core and the shell may have a concentration gradient in which a concentration of elements of the shell decreases closer to a center thereof. The semiconductor nanocrystal may have a structure including one semiconductor nanocrystal core and a multilayered shell surrounding the semiconductor nanocrystal core. In an embodiment, the multilayered shell may have two or more layers, such as two, three, four, five, or more layers. The two adjacent layers of the shell may have a single composition or different compositions. Each layer in the multilayered shell may have a composition that varies depending on a distance from the center.

The quantum dot may have a full width at half maximum (FWHM) of the light-emitting wavelength spectrum that is equal to or less than about 45 nm, or equal to or less than about 40 nm, or equal to or less than about 30 nm, and in this range, color purity or color reproducibility may be improved. Since light emitted by the quantum dot is emitted in all directions, a viewing angle of light may be improved.

In the quantum dot, a shell material and a core material may have different energy bandgaps. For example, the energy bandgap of the shell material may be larger than that of the core material. In another embodiment, the energy bandgap of the shell material may be smaller than that of the core material. The quantum dot may have a multilayered shell. In the multilayered shell, the energy bandgap of an outer layer may be larger than that of an inner layer (i.e., a layer closer to the core). In the multilayered shell, the energy bandgap of the outer layer may be smaller than the energy bandgap of the inner layer.

The quantum dot may control an absorption/emission wavelength by controlling a composition and size thereof. A maximum emission peak wavelength of the quantum dot may have a wavelength range of ultraviolet rays to infrared rays or higher.

The quantum dot may include an organic ligand (e.g., having a hydrophobic moiety and/or a hydrophilic moiety). The organic ligand moiety may be bonded to a surface of the quantum dot. The organic ligand may include RCOOH, $RNH_2$, $R_2NH$, $R_3N$, RSH, $R_3PO$, $R_3P$, ROH, RCOOR, $RPO(OH)_2$, RHPOOH, $R_2POOH$, or a combination thereof, wherein each R may independently indicate a C3 to C40 (e.g., C5 or more and C24 or less) substituted or unsubstituted alkyl, a C3 to C40 substituted or unsubstituted aliphatic hydrocarbon group such as a substituted or unsubstituted alkenyl, a C6 to C40 (e.g., C6 or more and C20 or less) substituted or unsubstituted aromatic hydrocarbon group such as a substituted or unsubstituted C6 to C40 aryl group, or a combination thereof.

Examples of the organic ligand may include a thiol compound such as methane thiol, ethane thiol, propane thiol, butane thiol, pentane thiol, hexane thiol, octane thiol, dodecane thiol, hexadecane thiol, octadecane thiol, or benzyl thiol; an amine such as methane amine, ethane amine, propane amine, butane amine, pentyl amine, hexyl amine, octyl amine, nonyl amine, decyl amine, dodecyl amine, hexadecyl amine, octadecyl amine, dimethyl amine, diethyl amine, dipropyl amine, tributylamine, and trioctylamine; a carboxylic acid compound such as methanic acid, ethanic acid, propanoic acid, butanoic acid, pentanoic acid, hexanoic acid, heptanoic acid, octanoic acid, dodecanoic acid, hexadecanoic acid, octadecanoic acid, oleic acid, and benzoic acid; a phosphine compound such as methyl phosphine, ethyl phosphine, propyl phosphine, butyl phosphine, pentyl phosphine, octyl phosphine, dioctyl phosphine, tributylphosphine, trioctylphosphine, and the like; a phosphine compound or an oxide compound thereof such as methyl phosphine oxide, ethyl phosphine oxide, propyl phosphine oxide, butyl phosphine oxide, pentyl phosphine oxide, tributyl phosphine oxide, octyl phosphine oxide, dioctyl phosphine oxide, trioctyl phosphine oxide, diphenyl phosphine, a triphenyl phosphine compound or an oxide compound thereof, or a C5 to C20 alkyl phosphinic acid such as hexylphosphinic acid, octylphosphinic acid, dodecanephosphinic acid, tetradecanephosphinic acid, hexadecanephosphinic acid, or octadecanephosphinic acid, but the disclosure is not limited thereto. The quantum dot may contain a hydrophobic organic ligand alone or as a mixture of one or more. The hydrophobic organic ligand (e.g., an acrylate group, a methacrylate group, etc.) may not contain a photopolymerizable moiety.

A second insulating layer P2 may be positioned on the first color conversion layer CCL1, the second color conversion layer CCL2, and the transmissive layer CCL3. The second insulating layer P2 may cover and protect the first color conversion layer CCL1, the second color conversion layer CCL2, and the transmissive layer CCL3, thereby preventing foreign particles from flowing into the first color conversion layer CCL1, the second color conversion layer CCL2, and the transmissive layer CCL3.

A first color filter CF1, a second color filter CF2, and a third color filter CF3 may be positioned on the second insulating layer P2.

The first color filter CF1 may transmit red light that has passed through a first color conversion layer CCL1 and absorb light of other wavelengths, thereby increasing purity of red light emitted to outside of the display device. The second color filter CF2 may transmit green light that has passed through the second color conversion layer CCL2 and absorb light of other wavelengths, thereby increasing purity of green light emitted to outside of the display device. The third color filter CF3 may transmit blue light passing through the transmissive layer CCL3 and absorb light of the other wavelengths, thereby increasing purity of blue light emitted to the outside of the display device.

A second light blocking layer BM2 may be positioned between the first color filter CF1, the second color filter CF2, and the third color filter CF3. The second light blocking layer BM2 may have a shape in which at least two of the first color filter CF1, the second color filter CF2, and the third color filter CF3 overlap.

Stacked Structure of Light-Emitting Device

A light emitting device in which a first electrode having a stacked structure of ITO/Ag/ITO, a first emission part, a first charge generating layer, a second emission part, a second electrode including Yb having a thickness of about 10 Å and AgMg having a thickness of about 100 Å, and a capping layer having a thickness of about 500 Å were sequentially stacked according to an embodiment was manufactured.

The first emission part may include a hole injection layer including HAT-CN having a thickness of about 50 Å, a hole transport layer including NPB having a thickness of about 250 Å and TCTA having a thickness of about 50 Å, an emission layer having a thickness of about 200 Å and including a host and a dopant material, a hole blocking layer including T2T having a thickness of about 50 Å, and an electron transport layer including TPM-TAZ and Liq having a thickness of about 250 Å.

The first charge generating layer may include an n-type charge generating layer by including compounds according to Examples 1 to 4 or compounds according to Comparative Examples 1 and 2 below. In Comparative Example 1, 1% Li was doped to form an n-type charge generating layer, and in Comparative Examples 2 and the Examples, an n-type charge generating layer was formed without doping Li.

The second emission part may include a hole injection layer including HAT-CN having a thickness of about 50 Å, a hole transport layer including NPB having a thickness of about 400 Å and TCTA having a thickness of about 50 Å, an emission layer having a thickness of about 200 Å and including a host and a dopant, a hole blocking layer including T2T having a thickness of about 50 Å, and an electron transport layer including TPM-TAZ and Liq having a thickness of about 350 Å.

A material used to form each layer is as follows.

HAT-CN

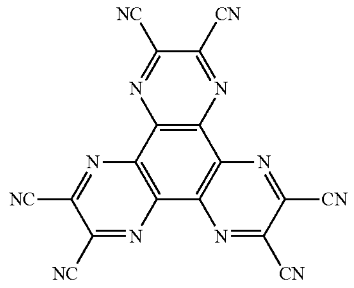

NFE

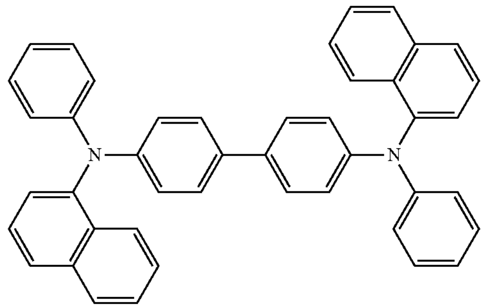

TCTA

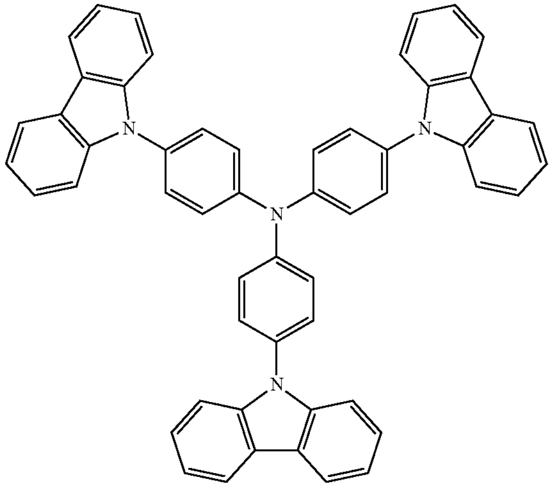

-continued

Host

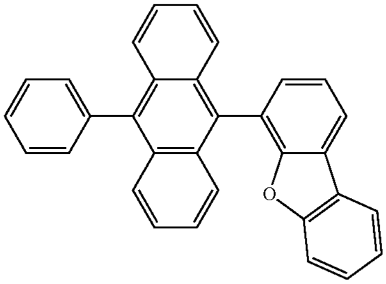

Dopant

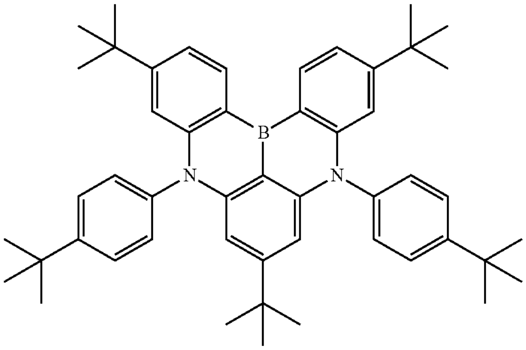

TBT

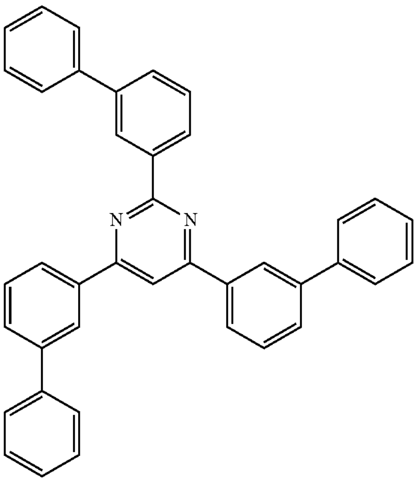

-continued

TBM-TAZ

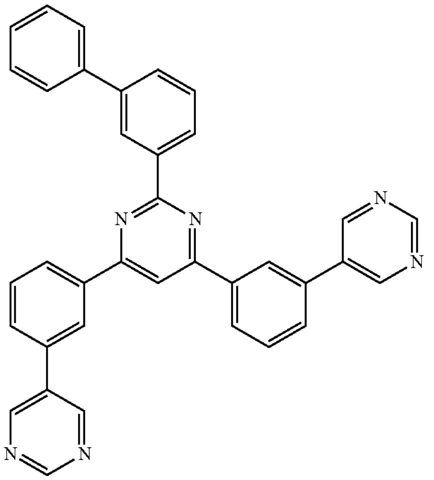

CPL

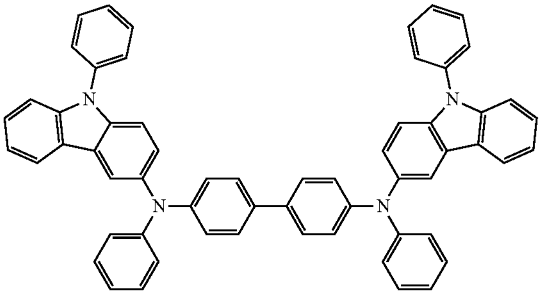

Hereinafter, an n-type charge generating layer including a compound according to Examples 1 to 4 will be described.

Example 1

After completely dissolving 9-(4-chloro-6-(9,9-dimethyl-9H-fluoren-3-yl)-1,3,5-triazin-2-yl)-9H-carbazole (5.00 g, 0.0106 mol), and 3-cyano phenylboronic acid ((3-cyanophenyl)boronic acid) (1.71 g, 0.0116 mol) in 200 mL of THF in a 500 mL round bottom flask in a nitrogen atmosphere, a 2M $K_2CO_3$ aqueous solution (100 mL) was added, and $Pd(PPh_3)_4$ (0.50 g, 3 mol %) was added, and refluxed for 8 hours. A reaction with $H_2O$ was terminated, and after extraction with $CH_2Cl_2$ and drying using anhydrous magnesium sulfate (anhydrous $MgSO_4$), a resultant was subjected to column chromatography using a solvent having a ratio of $CH_2Cl_2$:n-hexane of 1:10 to prepare a compound according to Example 1 (5.32 g, 85%).

H-NMR ($CdCl_3$): 8.57-8.55 (2H, m), 8.19-8.17 (2H, m), 8.02 (1H, d), 7.94-7.85 (3H, m), 7.74-7.68 (3H, m), 7.55-7.50 (3H, m), 7.38-7.16 (5H, m), 1.65 (6H, s), $C_{37}H_{25}N_5$ m/z: 539.21

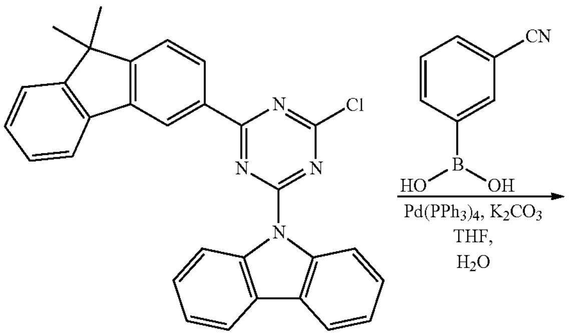

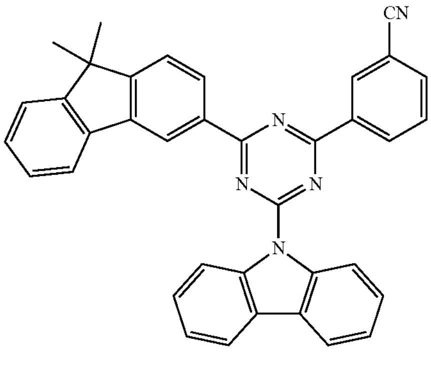

Example 2

A compound according to Example 2 (4.91 g, 82%) was prepared by reacting 9-(4-chloro-6-(9,9-dimethyl-9H-fluoren-3-yl)-1,3,5-triazin-2-yl)-9H-carbazole (5.00 g, 0.0106 mol), and 3,5-dicyanophenyl boronic acid ((3,5-dicyanophenyl) boronic acid) (2.00 g, 0.0116 mol) in the same manner as in Example 1.

H-NMR ($CdCl_3$): 8.55 (1H, d), 8.19-8.13 (4H, m), 7.94-7.89 (3H, m), 7.74-7.68 (2H, m), 7.55-7.50 (3H, m), 7.39-7.15 (5H, m), 1.65 (6H, s), $C_{38}H_{24}N_6$ m/z: 539.21

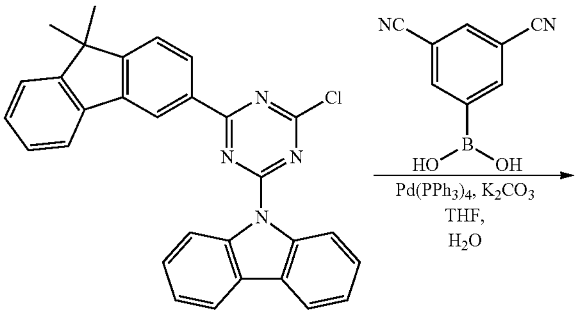

-continued

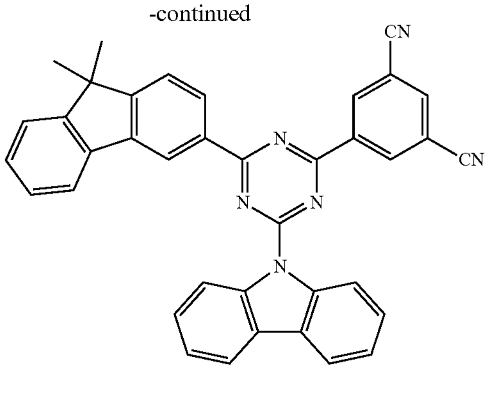

Example 3

A compound according to Example 3 (4.32 g, 80%) was prepared by reacting 9-(4-chloro-6-(9,9-dimethyl-9H-fluoren-3-yl)-1,3,5-triazin-2-yl)-9H-carbazole-3-carbonnitrile (5.00 g, 0.0100 mol), and phenylboronic acid (1.35 g, 0.0110 mol) in the same manner as in Example 1.

H-NMR ($CdCl_3$): 8.55 (1H, d), 8.36 (2H, d), 8.18 (1H, s), 7.94-7.90 (2H, m), 7.80-7.68 (4H, m), 7.55-7.50 (4H, m), 7.38-7.26 (4H, m), 7.16 (1H, t), 1.65 (6H, s), C37H25N5 m/z: 540.21

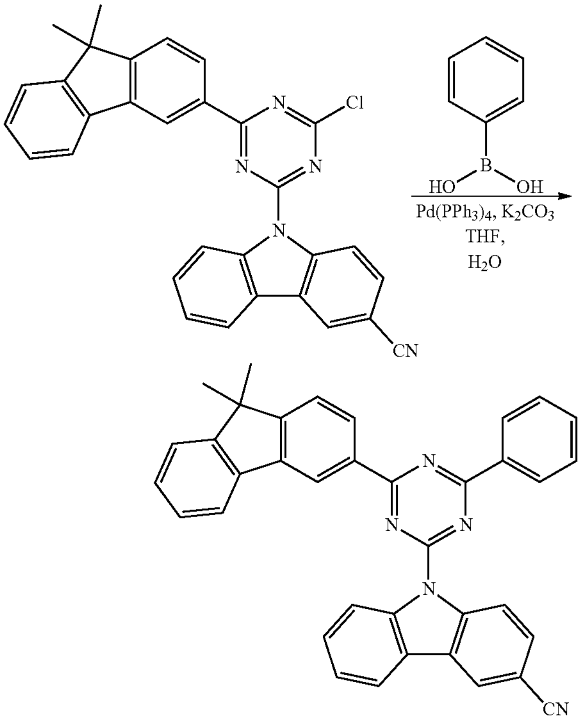

Example 4

A resultant (4.23 g, 75%) was prepared by reacting 9-(4-chloro-6-(9,9-dimethyl-9H-fluoren-3-yl)-1,3,5-triazin-2-yl)-9H-carbazole-3-carbonitrile (5.00 g, 0.0100 mol), and 3-cyanophenyl boronic acid (1.61 g, 0.0110 mol) in the same manner as in Example 1.

H-NMR ($CdCl_3$): 8.56-8.55 (2H, m), 8.18 (1H, s), 8.02 (1H, d), 7.90-7.68 (8H, m), 7.55 (1H, m), 7.38-7.28 (4H, m), 7.16 (1H, t), 1.65 (6H, s), C38H24N6 m/z: 564.21

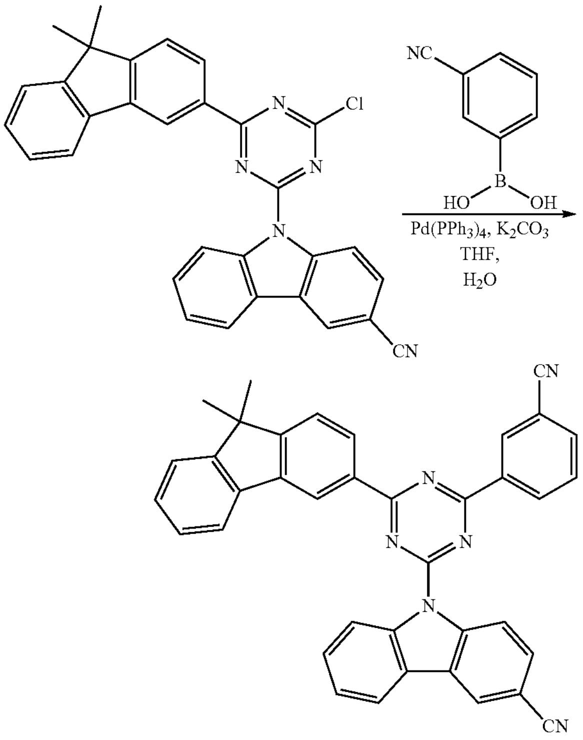

Comparative Example 1 and Comparative Example 2

The light-emitting device according to Comparative Example 1 may include the following compound, and may include an n-type charge generating layer having a thickness of about 50 Å. The light-emitting device according to Comparative Example 2 may include the following compound, and may include an n-type charge generating layer having a thickness of about 50 Å.

Comparative Example 1 Comparative Example 2

The compounds according to Examples 1 to 4 and Comparative Example 1 and Comparative Example 2 were analyzed using a differential pulse voltammetry (DPV) method in a methylene chloride solvent.

A Single Channel Electrochemical Workstation ZIVE SP2 was used for a measurement equipment. A dipole moment was calculated using a density functional theory (DFT theory).

TABLE 1

| | HOMO Energy level | LUMO Energy level | Eg (HOMO energy level − LUMO Energy level | Dipole moment |
|---|---|---|---|---|
| Comparative Example 1 | −5.63 | −2.35 | −3.28 | 0.8 |
| Comparative Example 2 | −5.71 | −2.60 | −3.11 | 1.8 |
| Example 1 | −5.90 | −2.96 | −2.94 | 3.7 |
| Example 2 | −6.02 | −3.31 | −2.71 | 6.4 |
| Example 3 | −6.01 | −2.88 | −3.13 | 5.4 |
| Example 4 | −6.20 | −3.21 | −2.99 | 7.0 |

Referring to Table 1, in the case of the n-type charge generating layer including the compound according to Examples 1 to 4, a LUMO energy level may be in a range of about −2.8 eV to about −3.4 eV. It was confirmed that the LUMO energy level could be lower than that of the n-type charge generating layer including the compound according to Comparative Examples 1 and 2. The n-type charge generating layer including the compound according to Examples 1 to 4 may have a higher dipole moment value than that of the n-type charge generating layer including the compound according to Comparative Examples 1 and 2. Accordingly, electrons may move readily from the p-type charge generating layer to the n-type charge generating layer.

Characteristics of the light-emitting device including the n-type charge generating layer were examined as shown in Table 2 below.

TABLE 2

| | Driving voltage (V) | Efficiency (Cd/A) | Lifespan (T95@100 nit) |
|---|---|---|---|
| Comparative Example 1 | 7.25 | 14.5 | 150 |
| Comparative Example 2 | 10.51 | 10.8 | 10 |
| Example 1 | 7.15 | 14.8 | 160 |
| Example 2 | 7.10 | 15 | 165 |
| Example 3 | 7.14 | 14.6 | 155 |
| Example 4 | 7.05 | 14.9 | 153 |

For a light-emitting device including an n-type charge generating layer including the compound according to Examples 1 to 4, it was confirmed that even in case that it did not contain an inorganic material such as Li, a driving voltage, efficiency, and lifespan of the device may be provided at a level that is similar to or higher than those of the light-emitting device including the n-type charge generating layer including the compound according to Comparative Example 1. Hereinafter, characteristics of light-emitting devices according to Examples 5 to 8 will be described with reference to Table 3.

TABLE 3

| | Driving voltage (V) | Efficiency (Cd/A) | Lifespan (T95@100 nit) |
|---|---|---|---|
| Comparative Example 1 | 7.25 | 14.5 | 150 |
| Example 1 | 7.15 | 14.8 | 160 |
| Example 5 | 7.05 | 14.8 | 162 |
| Example 6 | 7.00 | 14.7 | 165 |
| Example 7 | 7.03 | 14.8 | 158 |
| Example 8 | 7.08 | 14.8 | 155 |

In Example 5, the n-type charge generating layer may be formed as a double layer, and the double n-type charge generating layer may include an n-type charge generating layer including the compound according to Example 1 disposed at a position close to the first light-emitting device, and an n-type charge generating layer including the compound according to Example 2 disposed at a position close to the second light-emitting device. In Example 6, the n-type charge generating layer may be formed as a double layer, and the double n-type charge generating layer may include an n-type charge generating layer including the compound according to Example 1 disposed at a position close to the first light-emitting device, and an n-type charge generating layer including the compound according to Example 4 disposed at a position close to the second light-emitting device.

In Example 7, the n-type charge generating layer may be formed as a double layer, and the double n-type charge generating layer may include an n-type charge generating layer including the compound according to Example 3 disposed at a position close to the first light-emitting device, while an n-type charge generating layer including the compound according to Example 2 is disposed at a position close to the second light-emitting device.

In Example 8, the n-type charge generating layer may be formed as a double layer, and the double n-type charge generating layer may include an n-type charge generating layer including the compound according to Example 3 disposed at a position close to the first light-emitting device, while an n-type charge generating layer including the compound according to Example 4 may be disposed at a position close to the second light-emitting device.

Referring to Table 3, it was confirmed that even in case that the n-type charge generating layer is provided in a double-layer structure as in Examples 5 to 8, similar levels of driving voltage, efficiency, and lifespan may be provided as compared to Comparative Example 1 and Example 1.

Hereinafter, characteristics of a light emitting device in case that an electron injection layer is formed using the compound according to Examples 1 to 4 will be described with reference to Table 4.

TABLE 4

| | Driving voltage (V) | Efficiency (Cd/A) | Lifespan (T95@100 nit) |
|---|---|---|---|
| Comparative Example 3 | 7.25 | 14.5 | 150 |
| Comparative Example 4 | 7.28 | 14.7 | 155 |
| Example 9 | 7.23 | 15.4 | 155 |
| Example 10 | 7.15 | 15.8 | 150 |
| Example 11 | 7.24 | 15.4 | 153 |
| Example 12 | 7.08 | 15.6 | 155 |

Example 9 may indicate a case where an electron injection layer is formed using the compound according to Example 1, Example 10 may indicate a case where an electron injection layer is formed using the compound according to Example 2, Example 11 may indicate a case where an electron injection layer is formed using the compound according to Example 3, and Example 12 may indicate a case where an electron injection layer is formed using the compound according to Example 4. Comparative Example 3 may use a light-emitting device including Yb and an electron injection layer having a thickness of about 10 Å, and Comparative Example 4 may use a light-emitting device including Liq and including an electron injection layer having a thickness of about 10 Å. Referring to Table 4, in the case of the light-emitting devices of Examples 9 to 12 in which the electron injection layer is formed with the compound represented by Chemical Formula 1, it was confirmed that the driving voltage, efficiency, and lifespan may be similar to those of a light-emitting device including an electron injection layer including a metal or an inorganic material.

The n-type charge generating layer according to an embodiment may include the compound represented by Chemical Formula 1. Since the n-type charge generating layer according to an embodiment does not include an inorganic material, it is possible to control a current leakage and unintentional light emission. A light-emitting device including an n-type charge generating layer according to an embodiment and a display panel including the same may improve display quality without color mixing.

While the disclosure has been described in connection with what is presently considered to be practical embodiments, it is to be understood that the disclosure is not limited to the disclosed embodiments, but, on the contrary, is intended to cover various modifications and equivalent arrangements included within the spirit and scope of the appended claims.

What is claimed is:

1. A light-emitting device comprising:

a first electrode;

a second electrode that overlaps the first electrode;

m emission parts positioned between the first electrode and the second electrode; and (m−1) charge generating layers disposed between adjacent m emission parts, wherein each of the charge generating layers includes an n-type charge generating layer and a p-type charge generating layer, the n-type charge generating layer includes a compound represented by Chemical Formula 1:

[Chemical Formula 1]

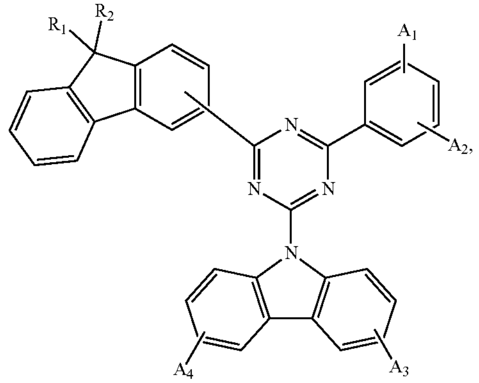

wherein in Chemical Formula 1, $R_1$ and $R_2$ each independently includes an aliphatic group, an aromatic group, or a hetero group having 1 to 30 carbon atoms, $A_1$, $A_2$, $A_3$, and $A_4$ each independently includes:

hydrogen, an aliphatic group, an aromatic group, or a hetero group; or an aliphatic group, an aromatic group, or a hetero group, each substituted with at least one of CN, F, or CF3, and m is a natural number that is greater than or equal to 2, and wherein when $A_4$ is an aromatic group, then at least one selected from among $A_1$, $A_2$, and $A_3$ is at least one of CN, F, or CF3.

2. The light-emitting device of claim 1, wherein the n-type charge generating layer does not contain an inorganic material.

3. The light-emitting device of claim 1, wherein a lowest unoccupied molecular orbital (LUMO) energy level of the n-type charge generating layer is in a range of about −2.8 eV to about −3.4 eV.

4. The light-emitting device of claim 1, wherein the compound represented by Chemical Formula 1 includes at least one of compounds represented by Chemical Formulas 1-1 to 1-4:

[Chemical Formula 1-1]

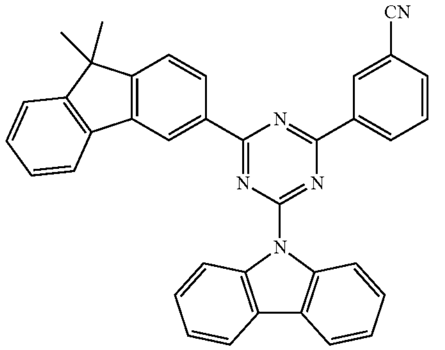

[Chemical Formula 1-2]

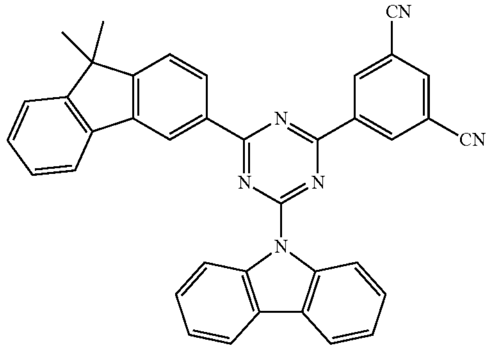

[Chemical Formula 1-3]

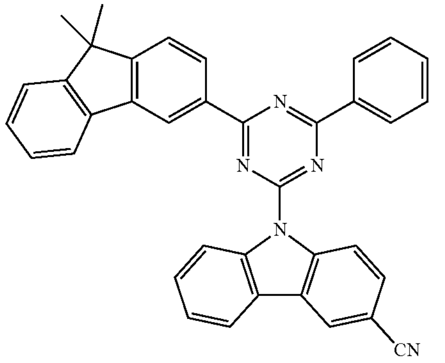

-continued

[Chemical Formula 1-4]

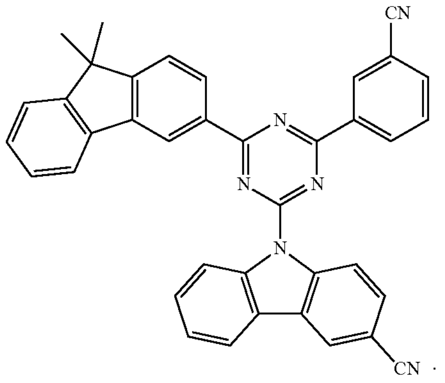

5. The light-emitting device of claim 1, wherein the n-type charge generating layer includes a first sub n-type charge generating layer and a second sub n-type charge generating layer.

6. The light-emitting device of claim 5, wherein each of the m emission parts includes a first emission part and a second emission part, the first sub n-type charge generating layer is positioned adjacent to the first emission part, and the second sub n-type charge generating layer is positioned adjacent to the second emission part.

7. The light-emitting device of claim 5, wherein a lowest unoccupied molecular orbital (LUMO) energy level value of the first sub n-type charge generating layer is greater than a LUMO energy level value of the second sub n-type charge generating layer.

8. A light-emitting device comprising:

a first electrode;

a second electrode that overlaps the first electrode;

m emission parts positioned between the first electrode and the second electrode; and (m−1) charge generating layers disposed between adjacent m emission parts, wherein each of the m emission parts includes a hole transport region, an electron transport region, and an emission layer positioned between the hole transport region and the electron transport region, the electron transport region includes a compound represented by Chemical Formula 1:

[Chemical Formula 1]

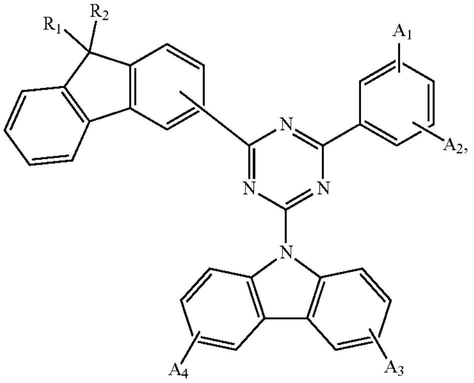

wherein in Chemical Formula 1, $R_1$ and $R_2$ each independently includes an aliphatic group, an aromatic group, or a hetero group having 1 to 30 carbon atoms, $A_1$, $A_2$, $A_3$, and $A_4$ each independently includes:

hydrogen, an aliphatic group, an aromatic group, or a hetero group; or an aliphatic group, an aromatic group, or a hetero group, each substituted with at least one of CN, F, or CF3, and m is a natural number that is greater than or equal to 2, and wherein when $A_4$ is an aromatic group, then at least one selected from among $A_1$, $A_2$, and $A_3$ is at least one of CN, F, or CF3.

9. The light-emitting device of claim 8, wherein the electron transport region includes an electron injection layer and an electron transport layer, and the electron injection layer includes the compound represented by Chemical Formula 1.

10. The light-emitting device of claim 9, wherein the electron injection layer does not contain an inorganic material.

11. The light-emitting device of claim 9, wherein a lowest unoccupied molecular orbital (LUMO) energy level of the electron injection layer is in a range of about −2.8 eV to about −3.4 eV.

12. A display device comprising:

a transistor positioned on a substrate; and a light-emitting device electrically connected to the transistor, wherein the light-emitting device includes:

a first electrode;

a second electrode that overlaps the first electrode;

m emission parts positioned between the first electrode and the second electrode; and (m−1) charge generating layers disposed between adjacent m emission parts, each of the charge generating layers includes an n-type charge generating layer and a p-type charge generating layer, the n-type charge generating layer includes a compound represented by Chemical Formula 1:

[Chemical Formula 1]

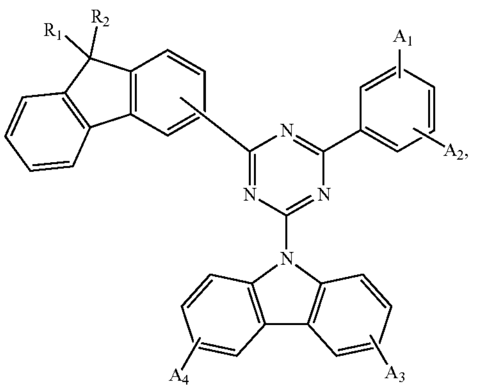

wherein in Chemical Formula 1, $R_1$ and $R_2$ each independently includes an aliphatic group, an aromatic group, or a hetero group having 1 to 30 carbon atoms, $A_1$, $A_2$, $A_3$, and $A_4$ each independently includes:

hydrogen, an aliphatic group, an aromatic group, or a hetero group; or an aliphatic group, an aromatic group, or a hetero group, each substituted with at least one of CN, F, or CF3, and m is a natural number that is greater than or equal to 2, and wherein when $A_4$ is an aromatic group, then at least one selected from among $A_1$, $A_2$, and $A_3$ is at least one of CN, F, or CF3.

13. The display device of claim 12, wherein the n-type charge generating layer does not contain an inorganic material.

14. The display device of claim 12, wherein a lowest unoccupied molecular orbital (LUMO) energy level of the n-type charge generating layer is in a range of about −2.8 eV to about −3.4 eV.

15. The display device of claim 12, wherein the n-type charge generating layer includes a first sub n-type charge generating layer and a second sub n-type charge generating layer.

16. The display device of claim 15, wherein each of the m emission parts includes a first emission part and a second emission part, the first sub n-type charge generating layer is positioned adjacent to the first emission part, and the second sub n-type charge generating layer is positioned adjacent to the second emission part.

17. The display device of claim 15, wherein a lowest unoccupied molecular orbital (LUMO) energy level value of the first sub n-type charge generating layer is greater than a LUMO energy level value of the second sub n-type charge generating layer.

18. The display device of claim 12, wherein the m emission parts include a hole transport region, an electron transport region, and an emission layer positioned between the hole transport region and the electron transport region, the electron transport region includes an electron injection layer and an electron transport layer, and the electron injection layer includes the compound represented by Chemical Formula 1.

* * * * *